US008591885B2

(12) United States Patent
Chang et al.

(10) Patent No.: US 8,591,885 B2
(45) Date of Patent: Nov. 26, 2013

(54) CARBONIC ANHYDRASE INHIBITOR SUSTAINED RELEASE INTRAOCULAR DRUG DELIVERY SYSTEMS

(75) Inventors: James N. Chang, Newport Beach, CA (US); Patrick M. Hughes, Aliso Viejo, CA (US); Gerald W. Devries, San Clemente, CA (US)

(73) Assignee: Allergan, Inc., Irvine, CA (US)

( * ) Notice: Subject to any disclaimer, the term of this patent is extended or adjusted under 35 U.S.C. 154(b) by 973 days.

(21) Appl. No.: 11/931,769

(22) Filed: Oct. 31, 2007

(65) Prior Publication Data

US 2011/0034448 A1 Feb. 10, 2011

Related U.S. Application Data

(63) Continuation-in-part of application No. 11/370,301, filed on Mar. 8, 2006, now abandoned, which is a continuation-in-part of application No. 11/364,687, filed on Feb. 27, 2006, now abandoned, and a continuation-in-part of application No. 11/116,698, filed on Apr. 27, 2005, now abandoned.

(60) Provisional application No. 60/721,600, filed on Sep. 28, 2005, provisional application No. 60/567,423, filed on Apr. 30, 2004.

(51) Int. Cl.
*A61K 39/395* (2006.01)
*C07K 16/22* (2006.01)
*A61K 9/51* (2006.01)
*A61K 9/22* (2006.01)
*A61K 31/54* (2006.01)
*A61K 31/63* (2006.01)

(52) U.S. Cl.
USPC ....... 424/130.1; 424/133.1; 514/23; 514/218; 514/222.8; 514/363; 514/9.3

(58) Field of Classification Search
None
See application file for complete search history.

(56) References Cited

U.S. PATENT DOCUMENTS

| | | |
|---|---|---|
| 4,200,098 A | 4/1980 | Ayer et al. |
| 4,281,654 A | 8/1981 | Shell et al. |
| 4,285,987 A | 8/1981 | Ayer et al. |
| 4,303,637 A | 12/1981 | Shell et al. |
| 4,304,765 A | 12/1981 | Shell et al. |
| 4,327,725 A | 5/1982 | Cortese et al. |
| 4,425,346 A | 1/1984 | Horlington |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,649,151 A | 3/1987 | Dougherty et al. |
| 4,656,186 A | 4/1987 | Bommer et al. |
| 4,668,506 A | 5/1987 | Bawa |
| 4,675,338 A | 6/1987 | Bommer et al. |
| 4,693,885 A | 9/1987 | Bommer et al. |
| 4,712,500 A | 12/1987 | Montandon |
| 4,853,224 A | 8/1989 | Wong |
| 4,863,457 A | 9/1989 | Lee |
| 4,865,846 A | 9/1989 | Kaufman |
| 4,866,168 A | 9/1989 | Dougherty et al. |
| 4,932,934 A | 6/1990 | Dougherty et al. |
| 4,935,498 A | 6/1990 | Sessler et al. |
| 4,959,217 A | 9/1990 | Sanders et al. |
| 4,968,715 A | 11/1990 | Dougherty et al. |
| 4,981,871 A | 1/1991 | Abelson |
| 4,997,652 A * | 3/1991 | Wong ............................. 424/428 |
| 5,002,962 A | 3/1991 | Pandey et al. |
| 5,017,579 A | 5/1991 | Gubin et al. |
| 5,019,400 A | 5/1991 | Gombotz et al. |
| 5,028,621 A | 7/1991 | Dougherty et al. |
| 5,034,413 A | 7/1991 | Chan et al. |
| 5,075,115 A | 12/1991 | Brine |
| 5,089,509 A | 2/1992 | Chandraratna |
| 5,093,349 A | 3/1992 | Pandey et al. |
| 5,100,431 A | 3/1992 | Buster et al. |
| 5,164,188 A | 11/1992 | Wong |
| 5,169,638 A | 12/1992 | Dennis et al. |
| 5,171,741 A | 12/1992 | Dougherty |
| 5,173,504 A | 12/1992 | Dougherty |

(Continued)

FOREIGN PATENT DOCUMENTS

| | | |
|---|---|---|
| CA | 1333770 | 1/1995 |
| EP | 0330451 | 8/1989 |

(Continued)

OTHER PUBLICATIONS

Stryer et al, in Biochemistry, Third edition, W H Freeman Company, New York, pp. 31-33, 1998.*
Tracy et al, Biomaterials 20: 1057-1062, 1999.*
Ngo et al, The Protein Folding Problem and Tertiary Structure Prediction, pp. 491-495, 1994.*
U.S. Appl. No. 10/837,143, filed Apr. 2004, Huang et al.
U.S. Appl. No. 10/340,237, filed Apr. 2004, Nivaggioli et al.
U.S. Appl. No. 10/836,880, filed Apr. 2004, Huang et al.
U.S. Appl. No. 10/836,904, filed Apr. 2004, Nivaggioli et al.
U.S. Appl. No. 10/836,908, filed Apr. 2004, Farooq.
U.S. Appl. No. 10/836,911, filed Apr. 2004, Huang et al.
U.S. Appl. No. 10/837,260, filed Apr. 2004, Hughes.

(Continued)

*Primary Examiner* — Phuong Huynh
(74) *Attorney, Agent, or Firm* — Laura L. Wine; Allergan, Inc.

(57) ABSTRACT

Biocompatible intraocular drug delivery systems include a carbonic anhydrase inhibitor therapeutic agent and a polymeric component in the form of an implant, a microparticle, a plurality of implants or microparticles, and combinations thereof. The therapeutic agent is released in a biologically active form, for example, the therapeutic agent may retain its three dimensional structure when released into an eye of a patient, or the therapeutic agent may have an altered three. The implants may be placed in an eye to treat or reduce the occurrence of one or more ocular conditions, such as retinal damage, including glaucoma and proliferative vitreoretinopathy among others.

5 Claims, 3 Drawing Sheets

(56) References Cited

U.S. PATENT DOCUMENTS

| | | | |
|---|---|---|---|
| 5,190,966 A | 3/1993 | Dougherty | |
| 5,198,460 A | 3/1993 | Pandey et al. | |
| 5,268,178 A | 12/1993 | Calhoun et al. | |
| 5,300,114 A | 4/1994 | Gwon et al. | |
| 5,300,499 A * | 4/1994 | Chow | 514/231.5 |
| 5,314,905 A | 5/1994 | Pandey et al. | |
| 5,356,629 A | 10/1994 | Sander et al. | |
| 5,385,887 A | 1/1995 | Yim et al. | |
| 5,438,071 A | 8/1995 | Clauss et al. | |
| 5,443,505 A | 8/1995 | Wong et al. | |
| 5,459,159 A | 10/1995 | Pandey et al. | |
| 5,466,233 A | 11/1995 | Weiner et al. | |
| 5,501,856 A | 3/1996 | Ohtori et al. | |
| 5,504,074 A | 4/1996 | D'Amato et al. | |
| 5,516,522 A * | 5/1996 | Peyman et al. | 424/426 |
| 5,587,371 A | 12/1996 | Sessler et al. | |
| 5,587,479 A | 12/1996 | Makovec et al. | |
| 5,597,897 A | 1/1997 | Ron et al. | |
| 5,655,832 A | 8/1997 | Pelka et al. | |
| 5,656,297 A | 8/1997 | Bernstein et al. | |
| 5,688,819 A | 11/1997 | Woodward et al. | |
| 5,707,643 A | 1/1998 | Ogura | |
| 5,766,242 A | 6/1998 | Wong et al. | |
| 5,770,589 A | 6/1998 | Billson et al. | |
| 5,776,699 A | 7/1998 | Klein et al. | |
| 5,798,349 A | 8/1998 | Levy et al. | |
| 5,824,072 A | 10/1998 | Wong | |
| 5,824,074 A | 10/1998 | Koch | |
| 5,844,099 A | 12/1998 | Stahl et al. | |
| 5,869,079 A | 2/1999 | Wong et al. | |
| 5,877,207 A | 3/1999 | Klein et al. | |
| 5,882,682 A | 3/1999 | Rork et al. | |
| 5,906,920 A | 5/1999 | Evans et al. | |
| 5,913,884 A | 6/1999 | Trauner et al. | |
| 5,919,970 A | 7/1999 | Song et al. | |
| 5,922,773 A | 7/1999 | Lipton et al. | |
| 5,958,954 A | 9/1999 | Klein et al. | |
| 6,034,221 A | 3/2000 | Berezenko et al. | |
| 6,051,576 A | 4/2000 | Ashton et al. | |
| 6,066,675 A | 5/2000 | Wen et al. | |
| 6,074,661 A | 6/2000 | Olejnik et al. | |
| 6,217,869 B1 | 4/2001 | Meyer et al. | |
| 6,217,895 B1 | 4/2001 | Guo et al. | |
| 6,225,303 B1 | 5/2001 | Miller et al. | |
| 6,258,319 B1 | 7/2001 | Hearst et al. | |
| 6,270,492 B1 | 8/2001 | Sinofsky | |
| 6,270,749 B1 | 8/2001 | Blumenkranz et al. | |
| 6,271,220 B1 | 8/2001 | Garst et al. | |
| 6,274,614 B1 | 8/2001 | Richter et al. | |
| 6,290,713 B1 | 9/2001 | Russell | |
| 6,294,361 B1 | 9/2001 | Horowitz et al. | |
| 6,306,426 B1 | 10/2001 | Olejnik et al. | |
| 6,317,616 B1 | 11/2001 | Glossop | |
| 6,319,273 B1 | 11/2001 | Chen et al. | |
| 6,329,836 B1 | 12/2001 | Drost et al. | |
| 6,331,313 B1 | 12/2001 | Wong et al. | |
| 6,357,568 B1 | 3/2002 | Chen | |
| 6,369,116 B1 | 4/2002 | Wong et al. | |
| 6,376,517 B1 | 4/2002 | Ross et al. | |
| 6,403,649 B1 | 6/2002 | Woodward et al. | |
| 6,455,062 B1 | 9/2002 | Olejnik et al. | |
| 6,482,854 B1 | 11/2002 | Lipton et al. | |
| 6,497,729 B1 | 12/2002 | Moussy et al. | |
| 6,537,568 B2 | 3/2003 | Olejnik et al. | |
| 6,548,078 B2 | 4/2003 | Guo et al. | |
| 6,565,871 B2 | 5/2003 | Kampinga et al. | |
| 6,573,280 B2 | 6/2003 | Dreyer | |
| 6,595,945 B2 | 7/2003 | Brown | |
| 6,699,493 B2 | 3/2004 | Wong | |
| 6,713,081 B2 | 3/2004 | Nussenblatt et al. | |
| 6,713,268 B2 | 3/2004 | Woodward et al. | |
| 6,726,918 B1 | 4/2004 | Wong et al. | |
| 6,765,012 B2 | 7/2004 | Andrews et al. | |
| 6,818,447 B1 | 11/2004 | Pavco et al. | |
| 6,835,202 B2 | 12/2004 | Harth et al. | |
| 6,890,546 B2 | 5/2005 | Mollison et al. | |
| 6,899,717 B2 | 5/2005 | Weber et al. | |
| 7,125,542 B2 | 10/2006 | Miller et al. | |
| 2003/0220376 A1 * | 11/2003 | Masferrer et al. | 514/359 |
| 2004/0170665 A1 | 9/2004 | Donovan | |
| 2005/0064010 A1 | 3/2005 | Cooper et al. | |
| 2006/0024350 A1 * | 2/2006 | Varner et al. | 424/427 |
| 2006/0073182 A1 * | 4/2006 | Wong et al. | 424/426 |
| 2007/0298073 A1 * | 12/2007 | Whitcup et al. | 424/427 |

FOREIGN PATENT DOCUMENTS

| | | |
|---|---|---|
| EP | 0361991 | 4/1990 |
| EP | 0364417 | 4/1990 |
| EP | 0430539 | 6/1991 |
| GB | 1372944 | 11/1994 |
| WO | WO 95/13765 | 5/1995 |
| WO | WO 96/38174 | 5/1996 |
| WO | WO 01/30323 | 5/2001 |
| WO | WO 01/58240 | 8/2001 |
| WO | WO 02/02076 | 1/2002 |
| WO | WO 02/43785 | 6/2002 |

OTHER PUBLICATIONS

U.S. Appl. No. 10/837,291, filed Apr. 2004, Nivaggioli et al.
U.S. Appl. No. 10/837,348, filed Apr. 30, 2004, Whitcup et al.
U.S. Appl. No. 10/837,356, filed Apr. 30, 2004, Huang et al.
U.S. Appl. No. 10/837,361, filed Apr. 30, 2004, Hughes et al.
U.S. Appl. No. 10/837,379, filed Apr. 30, 2004, Shiah et al.
U.S. Appl. No. 60/567,339, filed Apr. 30, 2004, Hughes et al.
U.S. Appl. No. 60/567,423, filed Apr. 30, 2004, Hughes et al.
Aiello, L.P., et al. "Vascular endothelial growth factor in Ocular fluid of patients with diabetic retinopathy and other retinal disorders", New Engl. J. of Med. 331: 1480-1487 (1994).
Anderson et al., "An Injectable Sustained Release Fertility Control System", Contraception vol. 13, pp. 375-384, (1976).
Baker, R., "Controlled Release of Biologically Active Agents", A Willey-Interseience Pub., p. 73-75 (1987).
Bito, L. Z. Biological Protection with Prostaglandins Cohen, M. M., ed., Boca Raton, Fla., CRC Press Inc., 1985, pp. 231-252.
Brubaker, "Mechanism of Action of Bimatoprost (Lumigan™)", *Surv Ophthalmol* 45 (Suppl 4): S347-S351 (2001).
Busse et al., "Tyrosine kinase inhibitors: rationale, mechanisms of action, and implications for drug resistance", Semin Oncol 28(suppl 16) 47-55 (2001).
Charles, et al., "Use of Bioerodible Polymers Impregnated with Mitomycin in Glaucoma Filtration Surgery in Rabbits," *Ophthalmology*, Apr. 1991, vol. 98, No. 4:503-508.
Chen et al., "Lumigan®: A Novel Drug for Glaucoma Therapy", *Optom in Pract*, 3:95-102 2002.
Cheng C. K. et al.."Intravitreal sustained-release dexamethasone device in the treatment of experimental uveitis", *Invest. Ophthalmol. Vis. Sci.* 36:442-53 (1995).
Chiang et al., "Pharmacokinetics and Intraocular Pressure Lowering Effect of Timolol Preparations in Rabbit Eyes," *Journal of Ocular Pharmacology and Therapeutics*, vol. 12, No. 4, pp. 471-480, (1996).
Company News on Call, "Oculex Announces Positive Clinical Results for Posurdex(R)—The First Biodegradable Ocular Implant in Clinical Trial", Copyright © 1996-2004 PR Newswire Association LLC.
Coleman et al., "A 3-Month Randomized Controlled Trial of Bimatoprost (LUMIGAN) versus Combined Timolol and Dorzolamide (Cosopt) in Patients with Glaucoma or Ocular Hypertension", *Ophthalmology* 110(12): 2362-8 (2003).
Connolly D.T., et al., "Tumor vascular permeability factor stimulates endothelial cell growth and angiogenesis" J. Clin. Invest 84: 1470-1478 (1989).
Conquelet et al, "Successful Photodynamic Therapy Combined with Laser Photocoagulation in Three Eyes with Classic Subfoveal Choroidal Neovascularization Affecting Two Patients with Multifocal Choroiditis: Case Reports", Bull. Soc. Belge Ophtalmol, 283, 69-73, 2002.

(56) References Cited

OTHER PUBLICATIONS

Di Colo, "Controlled drug release from implantable matrices based on hydrophobic polymers",*Biomaterials*, vol. 13, No. 12, pp. 850-856 (1992).
David L. Epstein, "Primary Open-Angle Glaucoma", *Chandler and Grant's Glaucoma*, Lea & Febiger, 1986, pp. 129-181.
Fabbro et al., "Protein tyrosine kinase inhibitors: new treatment modalities?", *Current Opinion in Pharmacology*, 2;374-381 (2002).
Fotsis, et. al., "The endogenous oestrogen metabolite 2-methoxyoestradiol inhibits angiogenesis and suppresses tumour growth", *Nature* 1994, 368, 237.
Gaudreault et al., "Preclinical pharmacokinetics of ranibizumab (rhuFabV2) after a single intravireal administration", IOVS, (2005); 460:726-733.
Gilman, A.G., et al., eds. (1990). *Goodman and Gilman's: The Pharmacological Basis of Therapeutics*. 8th Edition, Pergamon Press: New York, pp. 1447-1451.
Goel et al., "Tyrosine Kinase Inhibitors: A Clinical Perspective", *Current Oncology Reports*, 4:9-19 (2002).
Guenther, Lyn C., "Optimizing Treatment with Topical Tazarotene", *Am. J. Clin. Dermotol.*, 2003: 4(3):197-202.
Haluska et al., "Receptor tyrosine kinase inhibitors", Current Opinion in Investigational Drugs, 2(2):280-286 (2001).
Hare et al., "Efficacy and safety of memantine, an NMDA-Type Open-Channel Blocker, for reduction of retinal injury associated with experimental glaucoma in rat and monkey", Surv Opthamol 45(Suppl 3): S284-S289 (2001).
Hashizoe, Mototane et. al. "Scleral Plug of BiodegadablePolymers for Controlled Drug Release in the Vitreous", *Arch Ophthalmol.* 1994;112 : 1380-1384.
Heller,"Biodegradable Polymers in Controlled Drug Delivery", in: *CRC Critical Reviews in Therapeutic Drug Carrier Systems*, vol. 1, (CRC Press, Boca Raton, FL, 1987), pp. 39-90.
Heller, *Hydrogels in Medicine and Pharmacy*, N. A. Peppes ed., vol. III, (CRC Press, Boca Raton, FL, 1987), pp. 137-149.
Hoyng et al., "Pharmacological Therapy for Glaucoma", Drugs, Mar. 2000, 59(3):411-34.
Hubbard et al., "Protein tyrosine kinase structure and function", Annu. Rev. Biochem., 69:373-98 (2000).
Jackanicz et al., "Polyactic Acid As a Biodegradable Carrier for Contraceptive Steriods" Contraception, vol. 8, No. 3:227-235 (1973).
Jampel, et al, "Glaucoma Filtration Surgery in Monkeys Using 5-Fluorouridine in Polyanhydride Disks," *Arch Ophthalmol.*, Mar. 1990, vol. 108:430-435.
Kimura, Hideya et. al. "A New Vitreal Drug Delivery System using an Implantable Biodegradable Polymeric Device", *Invest Ophthalmol Vis Sci.* 1994;35 : 2815-2819.
Kobayashi, K., et al., "The Ddevelopment of recombinant human serum albumin", Ther Apher 1998 No. 2(4):257-62.
Kochinke et al., "Biodegradable Drug Delivery System for Uveitis Treatment", *Investigative Ophthalmology & Visual Science*, Feb. 15, vol. 37, No. 3, (1996).
Kwak, H.W. and D'Amico, D. J. "Evaluation of the retinal toxicity and pharmacokinetics of dexamethasone after intravitreal injection", *Arch. Ophthalmol.* 110:259-66 (1992).
Lai et al, "Alpha-2 adrenoceptor agonist protects retinal function after acute retinal ischemic injury in the rat", *Vis Neurosci*, 19:175-185 (2002).
Lee et al., "Glaucoma Filtration Surgery in Rabbits Using Bioerodible Polymers and 5-Fluorouacil", *Ophthalmology*, Dec. 1987, vol. 94, No. 12, pp. 1523-1530.
Lee et al., "The Use of Bioerodible Polymers and 5-Fluorouracil in Glaucoma Filtration Surgery," *Investigative Ophthalmology & Visual Science*, Nov. 1988, vol. 29, No. 11:1692-1697.
"Lumigan®: a new ocular hypotensive agent for achieving target intraocular pressures," Acta Ophthalmol Scand, Scientific Abstracts 2002; 80(4):457 (2002).
"Lumigan found effective in early phase 3", Ocul. Surg. News Mar. 1, 2001;19(5):1,35.

Marks, R., "Topical Tazarotene: Review and Re-Evaluation", *Retinoids*, 2001; 17(3):72-74.
Maurice, D.M. "Micropharmaceutics of the eye", *Ocular Inflammation Ther*. 1:97-102 (1983).
Maurice et al., Handbook of Experimental Pharmacology: Pharmacology of the Eye, M.L. Sears, Eds. vol. 69 (Spring-Verlag, Berlin-Haidelberg), pp. 19-116 (1986).
Miller et al., "Degradation Rates of Oral Resorbable Implants (Polylactates and Polyglycolates) : Rate Modification with Changes in PLA/PGA Copolymer Ratios", *J. Biomed. Materials Res.* vol. 11, pp. 711-719 (1977).
Miller et al., "Synthesis and Structure-Activity Profiles of A-Homoestranes, the Estratopones", J. Med. Chem., 40:3836-3841 (1997).
Mustonem, T., et al. "Endothelial receptor tyrosine Kinases involved in angiogenesis", J. Cell Biol. 129: 895-898 (1995).
Ohtani, W et al., "Physicochemical and immunochemical properties of recombinant human serum albumin from *Pichia pastoris*" Anal Biochem Feb. 1, 1998:256(1):56-62.
Olsen, T.W. et al. "Human scleral permeability: effects of age, cryotherapy, transscleral diode laser, and surgical thinning", *Invest. Ophthalmol. Vis. Sci.* 36:1893-1903 (1995).
Peters, T., Jr., All about Albumin Biochemistry, Genetics and Medical Applications, Academic Press (1996), pp. 295-298.
Phillips et al., "Efficacy of 0.1% Tazarotene Cream for the Treatment of Photodamage", *Arch Dermatol*, Nov. 2002, 138(11): 1486-1493.
Phillips et al., "Penetration of timolol eye drops into human aqueous humour: the first hour", *British Journal of Ophthalmology*, vol. 69, pp. 217-218 (1985).
Pribluda et al., "2-Methoxyestradiol: An endogenous antiangiogenic and antiproliferative drug candidate", *Cancer and Metastasis Reviews*, 19: 173-179 (2000).
*Physician's Desk Reference*, product information on "Alphagan®P", 54 Edition, (2000) pp. 493-494.
*Physician's Desk Reference for Ophthalmic Medicines*, 30 Edition, (2002) p. 285.
Quigley et al., "The mechanism of optic nerve damage in experimental acute intraocular pressure elevation", *Invest. Ophthalmol. Vis. Sci.* 19:505 (1980).
Rao, N.A. et al. (1997). "Intraocular inflammation and uveitis", in: *Basic and Clinical Science Course* (San Francisco: American Academy of Ophthalmology, 1997-1998), Section 9, pp. 57-80, 102-103, 152-156.
Renfro, L. et al. "Ocular effects of topical and systemic steroids", *Dermatologic Clinics* 10:505-12 (1992).
Schuettauf et al., "Effects of anti-glaucoma medications on ganglion cell survival: the DBA/2J mouse model", *Vision Res.*, 42(20):2333-7 (2002).
Schumacher et al., "The Physiological Estrogen Metabolite 2-methoxyestradiol reduced tumor growth and induces apoptosis in human solid tumors", *J Cancer Res Clin Oncol.*, 127:405-410 (2001).
Schwartz, B. "The response of ocular pressure to corticosteroids", *Ophthalmol. Clin. North Am.* 6:929-89 (1966).
Skalka, H.W. et al. "Effect of corticosteroids on cataract formation", *Arch. Ophthalmol.* 98:1773-7 (1980).
Smith et al., "Sustained-Release Subconjunctival 5-Fluorouracil", *Ophthalmic Surgery and Laser*, Sep. 1996, vol. 27, No. 9, pp. 763-767.
Surv Ophthalmol 2002; 47(3): p. 295.
Starr, M. S., "Further Studies on the Effect of Prostaglandin on Intraocular Pressure in the Rabbit", *Exp. Eye Res.*, vol. 11, pp. 170-177 (1971).
Siebold et al., *Prodrug* 5, 3 (1989).
"Tazarotene", *Drugs Future*, 2003; 28(2):208-209. Annual Update 2003: Dermatologic Drugs.
Tracy et al., "Factors affecting the degradation rate of poly(lactide-co-glycolide) microspheres in vivo and in vitro", *Biomaterials*, vol. 20, pp. 1057-1062 (1999).
USP 23; NF 18 (1995) pp. 1790-1798.
Watson et al., "A Six-month, Randomized, Double-masked Study Comparing Latanoprost with Timolol in Open-angle Glaucoma and Ocular Hypertension", *Ophthalmology* vol. 103:126-137 (1996).

(56) References Cited

OTHER PUBLICATIONS

Wheeler, "Experimental studies of agents with potential neuroprotective properties", Acta Ophthalmol Scand, 77(229):27-28 (1999).

Wheeler et al, "Role of Alpha-2 Agonists in Neuroprotection", Surv Ophthalmol, vol. 48 (Suppl 1): S47-S51 (Apr. 2003).

WoldeMussie, "Neuroprotection of retinal ganglion cells in experimental models of glaucoma", Minerva Oftalmol, 42(2):71-8 (2000).

WoldeMussie et al., "Neuroprotective effects of memantine in different retinal injury models in rats", J Glaucoma 11(6):474-480 (2002).

Woodward et al., AGN 192024 (Lumigan®): A Synthetic Prostamide Analog that Lowers Primate Intraocular Pressure by Virtue of Its Inherent Pharmacological Activity, ARVO 2002;(CD-ROM):POS.

Woodward et al., The Pharmacology of Bimatoprost (Lumigan™), Surv Ophthalmol 45 (Suppl 4) S337-S345 (2001).

Alphagan® Product Information, Allergan, Inc., Irvine, CA 92612, USA, 2005, pp. 1-10.

Encyclopedia of Polymer Science, "Injection Molding to Polysulfides," vol. 3, 2003, Table of Contents Only.

A Handbook of Common Polymers, Fibres, Films, Plastics and Rubbers, 1971, Table of Contents Only.

Tazorac® Product Information, Allergan, Inc., Irvine, CA 92612, USA, Jan. 2004, pp. 1-8.

Zhou et al, "Development of a multiple drug delivery implant for intraocular management of proliferative Vitreoretinopathy", Journal of Controlled Release, 1998, 55: pp. 281-295.

* cited by examiner

Figure 3

Variable Heavy

```
A.4.6.1    EIQLVQSGPELKQPGETVRISCKASGYTETNYGMNWVKQAPGKGLKWMG
              *   ** *   *** *  *                  *    * *
F(ab)-12   EVQLVESGGGLVQPGGSLRLSCAASGYTFTNYGMNWVRQAPGKGLEWVG
                                  *  ** * *                *
hum III    EVQLVESGGGLVQPGGSLRLSCAASGFTFSSYAMSWVRQAPGKGLEWVS
           1         10        20        30        40

A.4.6.1    WINTYTGEPTYAADFKRRFTFSLETSASTAYLQISNLKNDDTATYFCAK
             *  *               *** ***      *  *
F(ab)-12   WINTYTGEPTYAADFKRRFTFSLDTSKSTAYLQMNSLRAEDTAVYYCAK
           * **** ***   *** *   * * *    *                *
hum III    VISGDGGSTYYADSVKGRFTISRDNSKNTLYLQMNSLRAEDTAVYYCAR
           50 a      60        70        80 abc     90

A.4.6.1    YPHYYGSSHWYFDVWGAGITVTVSS
                         * *
F(ab)-12   YPHYYGSSHWYFDVWGQGTLVTVSS
           *             *
hum III    G-----------FDYWGQGTLVTVSS
                             110
```

Variable Light

```
A.4.6.1    DIQMTQTTSSLSASLGDRVIISCSASQDISNYLNWYQQKPDGTVKVLIY
              **       *   * *                      ****
F(ab)-12   DIQMTQSPSSLSASVGDRVTITCSASQDISNYLNWYQQKPGCAPKVLIY
                             *  **        *               *
humKI      DIQMTQSPSSLSASVGDRVTITCRASQSISNYLAWYQQKPGCAPKLLIY
           1         10        20        30        40

A.4.6.1    FTSSLHSGVPSRFSGSGSGTDYSLTISNLEPEDIATYYCQQYSTVPWTF
                                 **    *   *
F(ab)-12   FTSSLHSGVPSRFSGSGSGTDFTLTISSLQPEDFATYYCQQYSTYPWTF
           ** *                                        ***
humKI      AASSLESGVPSRFSGSGSGTDFTLTISSLQPEDFATYYCQQYNSLPWTF
                50        60        70        80        90

A.4.6.1    GGGTKLEIKR
              *  *
F(ab)-12   GQGTKVEIKR humKI      GQGTKVBIKR
           100
```

Fig. 3. Amino acid sequence of variable heavy and light domains of muMAb VEGF A.4.6.1, humanized F(ab) with optimal VEGF binding [F(ab)-12] and human consensus frameworks (humIII, heavy subgroup III; humk1, light k subgroup I). Asterisks, differences between humanized F(ab)-12 and the murine MAb or between F(ab)-12 and the human framework. CDRs are underlined.

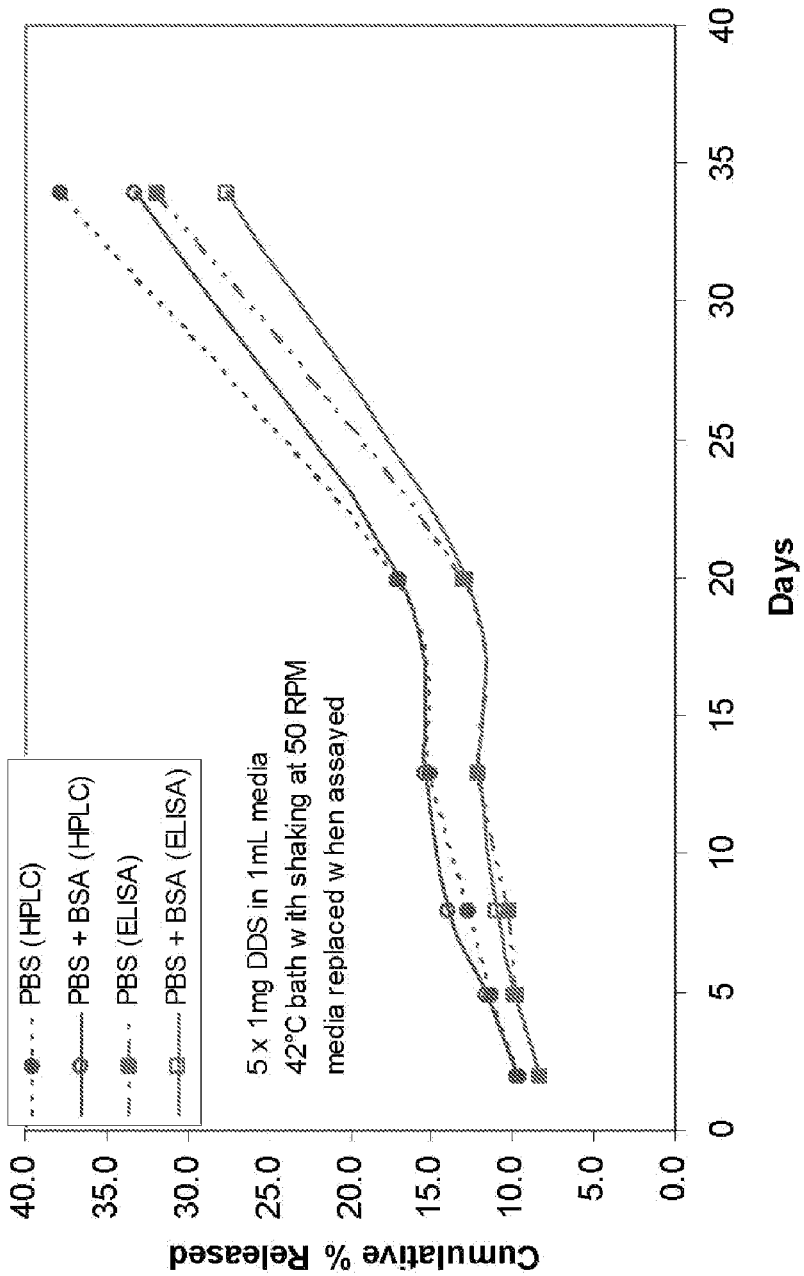

SEQUENCE LISTING

```
<160> NUMBER OF SEQ ID NOS: 23

<210> SEQ ID NO 1
<211> LENGTH: 19
<212> TYPE: RNA
<213> ORGANISM: Artificial sequence
<220> FEATURE:
<223> OTHER INFORMATION: siRNA

<400> SEQUENCE: 1
gcgauggccu cuucuguaa                                                19
```

```
<210> SEQ ID NO 2
<211> LENGTH: 19
<212> TYPE: RNA
<213> ORGANISM: Artificial sequence
<220> FEATURE:
<223> OTHER INFORMATION: siRNA

<400> SEQUENCE: 2
ccaugucucg gguccauuu                                                    19

<210> SEQ ID NO 3
<211> LENGTH: 19
<212> TYPE: RNA
<213> ORGANISM: Artificial sequence
<220> FEATURE:
<223> OTHER INFORMATION: siRNA

<400> SEQUENCE: 3
gcuuuacuau ucccagcua                                                    19

<210> SEQ ID NO 4
<211> LENGTH: 19
<212> TYPE: RNA
<213> ORGANISM: Artificial sequence
<220> FEATURE:
<223> OTHER INFORMATION: siRNA

<400> SEQUENCE: 4
gggaauaccc uucuucgaa                                                    19

<210> SEQ ID NO 5
<211> LENGTH: 19
<212> TYPE: RNA
<213> ORGANISM: Artificial sequence
<220> FEATURE:
<223> OTHER INFORMATION: siRNA

<400> SEQUENCE: 5
gcaucagcau aagaaacuu                                                    19

<210> SEQ ID NO 6
<211> LENGTH: 19
<212> TYPE: RNA
<213> ORGANISM: Artificial sequence
<220> FEATURE:
<223> OTHER INFORMATION: siRNA

<400> SEQUENCE: 6
gcugacaugu acggucuau                                                    19

<210> SEQ ID NO 7
<211> LENGTH: 19
<212> TYPE: RNA
<213> ORGANISM: Artificial sequence
<220> FEATURE:
<223> OTHER INFORMATION: siRNA

<400> SEQUENCE: 7
ggaauugaca agacagcaa                                                    19

<210> SEQ ID NO 8
<211> LENGTH: 19
<212> TYPE: RNA
<213> ORGANISM: Artificial sequence
<220> FEATURE:
<223> OTHER INFORMATION: siRNA
```

<400> SEQUENCE: 8
ccacuuaccu gaggagcaa                                               19

<210> SEQ ID NO 9
<211> LENGTH: 19
<212> TYPE: RNA
<213> ORGANISM: Artificial sequence
<220> FEATURE:
<223> OTHER INFORMATION: siRNA

<400> SEQUENCE: 9
gcuccugaag aucuguaua                                               19

<210> SEQ ID NO 10
<211> LENGTH: 19
<212> TYPE: RNA
<213> ORGANISM: Artificial sequence
<220> FEATURE:
<223> OTHER INFORMATION: siRNA

<400> SEQUENCE: 10
gcacgaaaua uccucuuau                                               19

<210> SEQ ID NO 11
<211> LENGTH: 576
<212> TYPE: DNA
<213> ORGANISM: Homo sapiens

<400> SEQUENCE: 11
atgaactttc tgctgtcttg ggtgcattgg agccttgcct tgctgctcta cctccaccat     60
gccaagtggt cccaggctgc acccatggca gaaggaggag ggcagaatca tcacgaagtg    120
gtgaagttca tggatgtcta tcagcgcagc tactgccatc caatcgagac cctggtggac    180
atcttccagg agtaccctga tgagatcgag tacatcttca gccatcctg tgtgcccctg     240 atgcgatgcg ggggctgctg caatgacgag ggcctggagt gtgtgccac tgaggagtcc    300 aacatcacca tgcagattat gcggatcaaa cctcaccaag gccagcacat aggagagatg    360
agcttcctac agcacaacaa atgtgaatgc agaccaaaga aagatagagc aagacaagaa    420
aatccctgtg ggccttgctc agagcggaga aagcatttgt ttgtacaaga tccgcagacg    480
tgtaaatgtt cctgcaaaaa cacagactcg cgttgcaagg cgaggcagct tgagttaaac    540
gaacgtactt gcagatgtga caagccgagg cggtga                             576

<210> SEQ ID NO 12
<211> LENGTH: 4071
<212> TYPE: DNA
<213> ORGANISM: Homo sapiens

<400> SEQUENCE: 12
atggagagca aggtgctgct ggccgtcgcc ctgtggctct gcgtggagac ccgggccgcc     60
tctgtgggtt tgcctagtgt ttctcttgat ctgcccaggc tcagcataca aaaagacata    120
cttacaatta aggctaatac aactcttcaa attacttgca ggggacagag ggacttggac    180 tggcttttggc ccaataatca gagtggcagt gagcaagggg tggaggtgac tgagtgcagc    240
gatggcctct tctgtaagac actcacaatt ccaaaagtga tcggaaatga cactggagcc    300
tacaagtgct tctaccggga aactgacttg gcctcggtca tttatgtcta tgttcaagat    360
tacagatctc catttattgc ttctgttagt gaccaacatg gagtcgtgta cattactgag    420
aacaaaaaca aaactgtggt gattccatgt ctcgggtcca tttcaaatct caacgtgtca    480

```
ctttgtgcaa gatacccaga aaagagattt gttcctgatg gtaacagaat ttcctgggac    540
agcaagaagg gctttactat tcccagctac atgatcagct atgctggcat ggtcttctgt    600
gaagcaaaaa ttaatgatga aagttaccag tctattatgt acatagttgt cgttgtaggg    660
tataggattt atgatgtggt tctgagtccg tctcatggaa ttgaactatc tgttggagaa    720
aagcttgtct taaattgtac agcaagaact gaactaaatg tggggattga cttcaactgg    780
gaatacccct tcttcgaagca tcagcataag aaacttgtaa accgagacct aaaaacccag    840
tctgggagtg agatgaagaa atttttgagc accttaacta tagatggtgt aacccggagt    900
gaccaaggat tgtacacctg tgcagcatcc agtgggctga tgaccaagaa gaacagcaca    960
tttgtcaggg tccatgaaaa acctttttgtt gcttttggaa gtggcatgga atctctggtg   1020
gaagccacgg tgggggagcg tgtcagaatc cctgcgaagt accttggtta cccaccccca   1080
gaaataaaat ggtataaaaa tggaataccc cttgagtcca atcacacaat taaagcgggg   1140
catgtactga cgattatgga agtgagtgaa agagacacag gaaattacac tgtcatcctt   1200
accaatccca tttcaaagga gaagcagagc catgtggtct ctctggttgt gtatgtccca   1260
ccccagattg gtgagaaatc tctaatctct cctgtggatt cctaccagta cggcaccact   1320
caaacgctga catgtacggt ctatgccatt cctcccccgc atcacatcca ctggtattgg   1380
cagttggagg aagagtgcgc caacgagccc agccaagctg tctcagtgac aaacccatac   1440
ccttgtgaag aatggagaag tgtggaggac ttccagggag gaaataaaat tgaagttaat   1500
aaaaatcaat ttgctctaat tgaaggaaaa aacaaaactg taagtaccct tgttatccaa   1560
gcggcaaatg tgtcagcttt gtacaaatgt gaagcggtca caaagtcgg gagaggagag    1620 agggtgatct ccttccacgt gaccaggggt cctgaaatta cttttgcaacc tgacatgcag   1680 cccactgagc aggagagcgt gtcttttgtgg tgcactgcag acagatctac gtttgagaac   1740
ctcacatggt acaagcttgg cccacagcct ctgccaatcc atgtgggaga gttgcccaca   1800 cctgttttgca agaacttgga tactctttgg aaattgaatg ccaccatgtt ctctaatagc   1860
acaaatgaca ttttgatcat ggagcttaag aatgcatcct tgcaggacca aggagactat   1920
gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
ggggaaagca tcgaagtctc atgcacggca tctgggaatc cccctccaca gatcatgtgg   2100
tttaaagata tgagaccctg tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca ttttcataa tagaaggtgc ccaggaaaag   2280
acgaacttgg aaatcattat tctagtaggc acggcggtga ttgccatgtt cttctggcta   2340
cttcttgtca tcatcctacg gaccgttaag cgggccaatg gaggggaact gaagacaggc   2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg cctttggcca agtgattgaa gcagatgcct ttggaattga caagacagca   2580
acttgcagga cagtagcagt caaaatgttg aaagaaggag caacacacag tgagcatcga   2640
gctctcatgt ctgaactcaa gatcctcatt catattggtc accatctcaa tgtggtcaac   2700
cttctaggtg cctgtaccaa gccaggaggg ccactcatgg tgattgtgga attctgcaaa   2760
tttggaaacc tgtccactta cctgaggagc aagagaaatg aatttgtccc ctacaagacc   2820
aaaggggcac gattccgtca agggaaagac tacgttggag caatccctgt ggatctgaaa   2880
```

-continued

```
cggcgcttgg acagcatcac cagtagccag agctcagcca gctctggatt tgtggaggag    2940
aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggacctggcg gcacgaaata tcctcttatc ggagaagaac    3120
gtggttaaaa tctgtgactt tggcttggcc cgggatattt ataaagatcc agattatgtc    3180
agaaaaggag atgctcgcct ccctttgaaa tggatggccc cagaaacaat ttttgacaga    3240
gtgtacacaa tccagagtga cgtctggtct tttggtgttt tgctgtggga aatattttcc    3300
ttaggtgctt ctccatatcc tggggtaaag attgatgaag aattttgtag gcgattgaaa    3360
gaaggaacta gaatgagggc ccctgattat actacaccag aaatgtacca gaccatgctg    3420
gactgctggc acggggagcc cagtcagaga cccacgtttt cagagttggt ggaacatttg    3480
ggaaatctct tgcaagctaa tgctcagcag gatggcaaag actacattgt tcttccgata    3540
tcagagactt tgagcatgga agaggattct ggactctctc tgcctacctc acctgtttcc    3600
tgtatggagg aggaggaagt atgtgacccc aaattccatt atgacaacac agcaggaatc    3660
agtcagtatc tgcagaacag taagcgaaag agccggcctg tgagtgtaaa aacatttgaa    3720
gatatcccgt tagaagaacc agaagtaaaa gtaatcccag atgacaacca gacggacagt    3780
ggtatggttc ttgcctcaga agagctgaaa actttggaag acagaaccaa attatctcca    3840
tcttttggtg gaatggtgcc cagcaaaagc agggagtctg tggcatctga aggctcaaac    3900
cagacaagcg gctaccagtc cggatatcac tccgatgaca cagacaccac cgtgtactcc    3960
agtgaggaag cagaactttt aaagctgata gagattggag tgcaaaccgg tagcacagcc    4020
cagattctcc agcctgactc ggggaccaca ctgagctctc ctcctgttta a             4071
```

```
<210> SEQ ID NO 13
<211> LENGTH: 21
<212> TYPE: DNA
<213> ORGANISM: Artificial sequence
<220> FEATURE:
<223> OTHER INFORMATION: siRNA

<400> SEQUENCE: 13
accucaccaa ggccagcact t                                                21

<210> SEQ ID NO 14
<211> LENGTH: 21
<212> TYPE: DNA
<213> ORGANISM: Artificial sequence
<220> FEATURE:
<223> OTHER INFORMATION: siRNA

<400> SEQUENCE: 14
gugcuggccu uggugaggut t                                                21

<210> SEQ ID NO 15
<211> LENGTH: 8
<212> TYPE: PRT
<213> ORGANISM: Artificial sequence
<220> FEATURE:
<223> OTHER INFORMATION: VEGF inhibitor

<400> SEQUENCE: 15

Lys Pro Ser Ser Pro Pro Glu Glu
1               5

<210> SEQ ID NO 16
<211> LENGTH: 123
```

```
<212> TYPE: PRT
<213> ORGANISM: Artificial sequence
<220> FEATURE:
<223> OTHER INFORMATION: anti-VEGF murine monoclonal antibody (variable
      region of heavy chain)

<400> SEQUENCE: 16

Glu Ile Gln Leu Val Gln Ser Gly Pro Glu Leu Lys Gln Pro Gly Glu
1               5                   10                  15

Thr Val Arg Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Tyr Ala Ala Asp Phe
    50                  55                  60

Lys Arg Arg Phe Thr Phe Ser Leu Glu Thr Ser Ala Ser Thr Ala Tyr
65                  70                  75                  80

Leu Gln Ile Ser Asn Leu Lys Asn Asp Asp Thr Ala Thr Tyr Phe Cys
                85                  90                  95

Ala Lys Tyr Pro His Tyr Tyr Gly Ser Ser His Trp Tyr Phe Asp Val
            100                 105                 110

Trp Gly Ala Gly Ile Thr Val Thr Val Ser Ser
        115                 120

<210> SEQ ID NO 17
<211> LENGTH: 123
<212> TYPE: PRT
<213> ORGANISM: Artificial sequence
<220> FEATURE:
<223> OTHER INFORMATION: humanized anti-VEGF F(ab) (vanriable region of
      heavy chain)

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 18
<211> LENGTH: 113
<212> TYPE: PRT
<213> ORGANISM: Artificial sequence
<220> FEATURE:
<223> OTHER INFORMATION: human consensus framework (variable region of
      heavy chain)

<400> SEQUENCE: 18

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Val Ile Ser Gly Asp Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Asp Tyr Trp Gly Gln Gly Thr Leu Val Thr Val Ser
            100                 105                 110

Ser

<210> SEQ ID NO 19
<211> LENGTH: 108
<212> TYPE: PRT
<213> ORGANISM: Artificial sequence
<220> FEATURE:
<223> OTHER INFORMATION: anti-VEGF murine mAb (variable region of light
      chain)

<400> SEQUENCE: 19

Asp Ile Gln Met Thr Gln Thr Thr Ser Ser Leu Ser Ala Ser Leu Gly
1               5                   10                  15

Asp Arg Val Ile Ile Ser Cys Ser Ala Ser Gln Asp Ile Ser Asn Tyr
            20                  25                  30

Leu Asn Trp Tyr Gln Gln Lys Pro Asp Gly Thr Val Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Thr Val Phe Trp
                85                  90                  95

Thr Phe Gly Gly Gly Thr Lys Leu Glu Ile Lys Arg
            100                 105

<210> SEQ ID NO 20
<211> LENGTH: 108
<212> TYPE: PRT
<213> ORGANISM: Artificial sequence
<220> FEATURE:
<223> OTHER INFORMATION: amanized anti-VEGF F(ab) (variable region of
      light chain)

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
```

```
                        85                  90                  95
Thr Phe Gly Gln Gly Thr Lys Val Glu Ile Lys Arg
                100                 105

<210> SEQ ID NO 21
<211> LENGTH: 108
<212> TYPE: PRT
<213> ORGANISM: Artificial sequence
<220> FEATURE:
<223> OTHER INFORMATION: human consensus framework (variable region of
      light chain)

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
                20                  25                  30

Leu Ala Trp Tyr Gln Gln Lys Pro Gly Lys Ala Pro Lys Leu Leu Thr
            35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg
                100                 105

<210> SEQ ID NO 22
<211> LENGTH: 21
<212> TYPE: DNA
<213> ORGANISM: Artificial sequence
<220> FEATURE:
<223> OTHER INFORMATION: siRNA

<400> SEQUENCE: 22
cugaguuuaa aaggcaccct t                                             21

<210> SEQ ID NO 23
<211> LENGTH: 21
<212> TYPE: DNA
<213> ORGANISM: Artificial sequence
<220> FEATURE:
<223> OTHER INFORMATION: siRNA

<400> SEQUENCE: 23
ttgacucaaa uuuuccgugg g                                             21
```

CARBONIC ANHYDRASE INHIBITOR SUSTAINED RELEASE INTRAOCULAR DRUG DELIVERY SYSTEMS

CROSS REFERENCE

This application is a continuation in part of U.S. patent application Ser. No. 11/370,301, filed Mar. 8, 2006, which is a continuation in part of application Ser. No. 11/364,687, filed Feb. 27, 2006, which claims priority to application Ser. No. 60/721,600, filed Sep. 28, 2005, and is a continuation in part of application Ser. No. 11/116,698, filed Apr. 27, 2005, which claims priority to application Ser. No. 60/567,423, filed Apr. 30, 2004. The contents of all of these applications are incorporated herein by reference in their entireties.

BACKGROUND

The present invention generally relates to devices and methods to treat an eye of a patient, and more specifically to drug delivery systems that provide extended release of a macromolecule therapeutic agent to an eye in which a device is placed, and to methods of making and using such devices, for example, to treat or reduce one or more symptoms of an ocular condition to improve or maintain vision of a patient.

Interest in the use of proteins and antibody fragments for treating ocular diseases has increased in recent years. One challenge with macromolecules is delivering them into the vitreous in close proximity to the retina. Another challenge is maintaining therapeutically effective amounts of such therapeutic macromolecules within the eye for sustained periods of time.

Intravitreal implants have been described which include non-macromolecule therapeutic agents. For example, U.S. Pat. No. 6,713,081 discloses ocular implant devices made from polyvinyl alcohol and used for the delivery of a therapeutic agent to an eye in a controlled and sustained manner. The implants may be placed subconjunctivally or intravitreally in an eye.

Biocompatible implants for placement in the eye have also been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; and 6,699,493. U.S. Patent Publication No. 20040170665 (Donovan) describes implants which include a Clostridial neurotoxin.

It would be advantageous to provide eye implantable drug delivery systems, such as intraocular implants, and methods of using such systems, that are capable of releasing a macromolecule therapeutic agent at a sustained or controlled rate for extended periods of time and in amounts with few or no negative side effects.

SUMMARY

The present invention provides new drug delivery systems, and methods of making and using such systems, for extended or sustained drug release into an eye, for example, to achieve one or more desired therapeutic effects. The drug delivery systems are in the form of implants or implant elements, or microparticles that may be placed in an eye. The present systems and methods advantageously provide for extended release times of one or more macromolecule therapeutic agents. Thus, the patient in whose eye the system has been placed receives a therapeutic amount of an agent for a long or extended time period without requiring additional administrations of the agent. For example, the patient has a substantially consistent level of therapeutically active agent available for consistent treatment of the eye over a relatively long period of time, for example, on the order of at least about one week, such as between about one and about twelve months after receiving an implant. Such extended release times facilitate obtaining successful treatment results while reducing problems associated with existing techniques.

Intraocular drug delivery systems in accordance with the disclosure herein comprise a therapeutic component and a drug release sustaining component associated with the therapeutic component. The therapeutic component comprises a non-neurotoxic macromolecule, and the drug release sustaining component comprises a biodegradable polymer, a non-biodegradable polymer, or combinations thereof.

Therapeutic Component

According to the present invention, the therapeutic component described herein comprises one or more macromolecular therapeutic agent. By "macromolecular" is meant that the agent consists of, consists essentially of, or comprises a peptide or oligonucleotide as such terms are defined herein.

Therapeutic agents according to the present invention include peptides, polypeptides, proteins, oligonucleotides, and nucleic acids. In particularly preferred embodiments of the invention, the therapeutic agent may comprise a protein, a polyclonal or monoclonal antibody, an antibody fragment, such as a monovalent fraction antigen-binding papain fragment (Fab) or a bivalent fraction antigen binding pepsin fragment (F'ab$_2$). Additionally, the antibodies or antibody fragments may be naturally occurring or genetically engineered. For example, the term "antibodies" may include chimeric antibodies comprising human $L_C$ and $H_C$ regions and $L_V$ and $H_V$ regions from another species, for example, from mouse cells. Chimeric antibodies are useful in the design of antibody-based drugs, since the use of unaltered mouse antibodies induces the production of human anti-mouse immunoglobulins and resultant clearance and reduction of efficacy.

However, chimeric antibodies, while having reduced immunogenicity as compared to the rodent antibody, do not solve all the problems that exist in the use of antibodies as drugs. For example, to minimize allotypic variation in the constant regions a human consensus sequence can be used representing the most common allotype in the general population. A further refinement has been used, called complimentarily determining region (CVDR) grafting. In this method, only the three antigen binding sites (formed by the three CDRs of the heavy chain and the three CDRs of the light chain) are excised from the murine antibodies and the nucleic acid regions encoding these CDRs have been inserted (or "grafted") into a nucleic acid coding sequence encoding the framework region of the human antibody.

Further refinements may comprise what has been termed "reshaping", "veneering" and "hyperchimerization". In reshaping, the rodent variable region is compared with the consensus sequence of the protein sequence subgroup to which it belongs, as is the human framework compared with a consensus of the framework sequence for the antibody family to which it belongs. This analysis can identify amino acid residues that may be the result of mutation during the affinity maturation process; these residues are called "idiosyncratic". By incorporating the more common human residues in these positions, immunogenicity problems resulting from the idiosyncratic residues can be minimized.

Humanization by hyperchimerization involves a comparison of the human and murine non-CDR variable region sequences and the one with the highest homology is selected as the acceptor framework. Again, idiosyncratic residues are replaced with more highly conserved human ones. Those non-CDR residues that may interact with the CDR residues are identified and inserted into the framework sequence.

Veneering involves determining the three dimensional conformation of a humanized murine antibody and replacing the expose surface amino acids with those commonly found in human antibodies. In the first step the most homologous human variable regions are selected and compared to the corresponding mouse variable regions. In the second step, the mouse framework residues differing from the human framework are replaced with the human residues; only those residues fully or partially exposed at the surface of the antibody are changed.

While the humanization of antibodies provides therapeutic advantages not available in the use of murine or chimeric antibodies alone, new classes of peptide and nucleic acid agents have been engineered to bind strongly to a desired target thereby antagonizing the normal activity of the target.

For example, fibronectins and fibronectin-related molecules (hereinafter collectively referred to as "fibronectins"), are multi-domain glycoproteins found in a soluble form in plasma, and in an insoluble form in loose connective tissue and basement membranes. They contain multiple copies of 3 repeat regions (types I, II and III), which bind to a variety of substances including heparin, collagen, DNA, actin, fibrin and fibronectin receptors on cell surfaces. Fibronectins are involved in a number of important functions: e.g., wound healing; cell adhesion; blood coagulation; cell differentiation and migration; maintenance of the cellular cytoskeleton; and tumor metastasis. The role of fibronectin in cell differentiation is demonstrated by the marked reduction in the expression of its gene when neoplastic transformation occurs. Cell attachment has been found to be mediated by the binding of the tetrapeptide RGDS to integrins on the cell surface although related sequences can also display cell adhesion activity.

Plasma fibronectin occurs as a dimer of 2 different subunits, linked together by 2 disulphide bonds near the C-terminus. The difference in the 2 chains occurs in the type III repeat region and is caused by alternative splicing of the mRNA from one gene.

The fibronectin type III (FnIII) repeat region is an approximately 100 amino acid domain, different tandem repeats of which contain binding sites for DNA, heparin and the cell surface. The superfamily of sequences believed to contain FnIII repeats represents 45 different families, the majority of which are involved in cell surface binding in some manner, or are receptor protein tyrosine kinases, or cytokine receptors.

Because a common characteristic of fibronectins is that they are involved in intermolecular binding, and due to the common scaffolding structure of the fibronectin molecule, such molecules are very useful templates for making and producing selective binding molecules capable of acting as antibody mimics. Such antibody mimics will often provide interference in preventing the interaction of the target "antigen" molecule or moiety with a binding partner, such as a selective or specific receptor. Thus, such selectively binding fibronectin molecules comprise ideal templates for making, for example, receptor antagonists.

The FnIII loops comprise regions that may be subjected to random mutation and directed evolutionary schemes of iterative rounds of target binding, selection, and further mutation in order to develop useful therapeutic tools. Fibronectin based "addressable" therapeutic binding molecules (hereinafter "FATBIMs") may be useful in the inhibition of certain ophthalmically deleterious ligands or receptors, such as VEGF. FATBIMs include the species of fibronectin-based binding molecules termed Adnectins by Compound Therapeutics, Inc.

Whether nucleic acid or polypeptide in nature, macromolecular therapeutic components present specific challenges when making controlled release intraocular drug delivery systems. Certain preferred drug delivery systems comprise, for example, a polymeric solid insertable drug delivery device. Preferably, such drug delivery systems are biodegradable, and are capable of being injected or surgically placed within the anterior or posterior segment of the mammalian eye.

In one embodiment, a sustained-release intraocular drug delivery system comprises a therapeutic component which comprises a non-neurotoxic macromolecule therapeutic agent; and a polymeric component associated with the therapeutic component to permit the therapeutic component to be released into the interior of an eye of an individual for at least about one week after the drug delivery system is placed in the eye.

In accordance with the present invention, the therapeutic component of the present systems can comprise, consist essentially of, or consist entirely of, anti-bacterial agents, anti-angiogenic agents, anti-inflammatory agents, neuroprotectant agents, growth factors, growth factor inhibitors, cytokines, intraocular pressure reducing agents, ocular hemorrhage therapeutic agents, and combinations thereof. For example, the therapeutic component may comprise, consist essentially of, or consist of, a therapeutic agent selected from the group consisting of peptides, proteins, antibodies, antibody fragments, and nucleic acids. More specifically, the drug delivery system may comprise short interfering ribonucleic acids (siRNAs, also referred to as Sirnas), oligonucleotide aptamers, VEGF or urokinase inhibitors. Some specific examples include one or more of the following: hyaluronic acid, a hyaluronidase, such as Vitrase, (ocular hemorrhage treatment compound), ranibizumab, bevacizumab, pegaptanib, such as Macugen, (VEGF inhibitors), rapamycin, and cyclosporine. Advantageously, the therapeutic agent is released in a biologically active form when the implant is placed in an eye.

The polymeric component of the present systems may comprise a polymer selected from the group consisting of poly-lactic acid (PLA), poly-glycolic acid (PGA), poly-lactide-co-glycolide (PLGA), polyesters, poly (ortho ester), poly(phosphazine), poly (phosphate ester), polycaprolactones, gelatin, collagen, derivatives thereof, and combinations thereof.

A method of making the present systems involves combining or mixing the therapeutic component with the polymeric component to form a mixture. The mixture may then be extruded or compressed to form a single composition. The single composition may then be processed to form individual implants or microparticles suitable for placement in an eye of a patient.

The implants may be placed in an ocular region to treat a variety of ocular conditions, such as treating, preventing, or reducing at least one symptom associated with glaucoma, or ocular conditions related to excessive excitatory activity or glutamate receptor activation or associated with, for example, retinal neurodegeneration, such as by apoptosis or necrosis, and angiogenesis, such as in conditions such as exudative and non-exudative age related macular degeneration. Placement of the implants may be through surgical implantation, or through the use of an implant delivery device which administers the implant via a needle or catheter. The implants can effectively treat conditions associated with neovascularization of the eye, such as the retina. The therapeutic component can be released at controlled or predetermined rates when the implant is placed in the eye. Such rates may range from about 0.003 micrograms/day to about 5000 micrograms/day.

Kits in accordance with the present invention may comprise one or more of the present systems, and instructions for using the systems. For example, the instructions may explain how to administer the implants to a patient, and types of conditions that may be treated with the systems.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description, examples, and claims, particularly when considered in conjunction with the accompanying drawings.

BRIEF DESCRIPTION OF THE DRAWINGS

FIG. 3 is a chart aligning and comparing the amino acid sequences of the variable regions of bevacizumab and showing several similar amino acid sequences in such variable region, including the variable regions (heavy chain) of a) a murine monoclonal anti VEGF IGg1 antibody, b) a humanized F(ab) fragment having optimized VEGF binding and c) the human consensus framework, as well as the variable regions (light chain) of d) a murine monoclonal anti VEGF IGg1 antibody, e) a humanized F(ab) fragment having optimized VEGF binding, and f) the human consensus framework.

FIG. 4 is a graph showing the release profile of an anti VEGF Fab fragment from a DDS, as described in Example 6A.

DESCRIPTION

Figure 1:
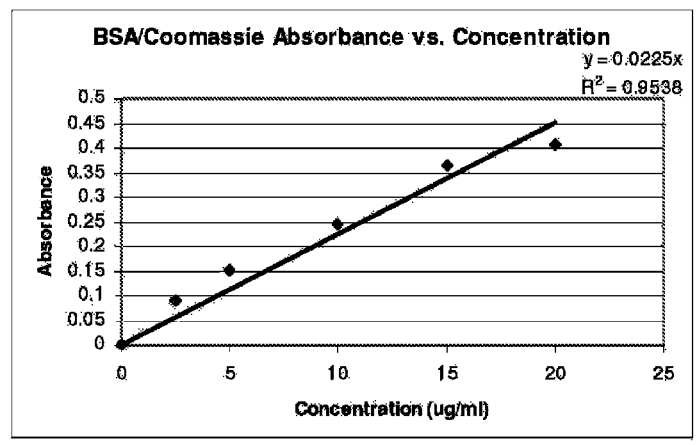
FIG. 1 is a graph illustrating absorbance vs. concentration for bovine serum albumin (BSA) with a coomassie reagent.

As described herein, controlled and sustained administration of one or more therapeutic agents through the use of one or more intraocular drug delivery systems, such as intraocular implants or polymeric particles, may effectively treat one or more undesirable ocular conditions. The present drug delivery systems comprise a pharmaceutically acceptable polymeric composition and are formulated to release one or more pharmaceutically active agents over an extended period of time, such as for more than one week, and in certain embodiments for a period of time of one year or more. In other words, the present drug delivery systems comprise a polymeric component and a therapeutic component. As described herein, the polymeric component can comprise one or more biodegradable polymers, one or more biodegradable copolymers, one or more non-biodegradable polymers, and one or more non-biodegradable copolymers, and combinations thereof. The polymeric component may be understood to be a drug release sustaining component. The therapeutic component of the present drug delivery systems comprises one or more macromolecule therapeutic agents. Thus, the therapeutic component may be understood to comprise a therapeutic agent other than small chemical compounds. Examples of suitable macromolecule therapeutic agents include peptides, proteins, nucleic acids, antibodies, and antibody fragments. For example, the therapeutic component of the present drug delivery systems may comprise, consist essentially of, or consist entirely of, one or more therapeutic agents selected from the group consisting of anti-angiogenesis compounds, ocular hemorrhage treatment compounds, macromolecular non-steroidal anti-inflammatory agents, growth factor inhibitors (e.g. VEGF inhibitors), growth factors, cytokines, antibodies, oligonucleotide aptamers, antisense oligonucleotides small interfering ribonucleic acid (siRNA) molecules and antibiotics. The present systems are effective to provide a therapeutically effective dosage(s) of the agent or agents directly to a region of the eye to treat, prevent, and/or reduce one or more symptoms of one or more undesirable ocular conditions. Thus, with each administration, therapeutic agents will be made available at the site where they are needed and will be maintained at effective concentrations for an extended period of time, rather than subjecting the patient to more frequent injections or, in the case of self-administered drops, ineffective treatment with only limited bursts of exposure to the active agent or agents or, in the case of systemic administration, higher systemic exposure and concomitant side effects or, in the case of non-sustained release dosages, potentially toxic transient high tissue concentrations associated with pulsed, non-sustained release dosing.

In a preferred embodiment the therapeutic components of the present invention may include polypeptide antibody mimics that comprise an "addressable" region analogous to an antibody variable region, as with the fibronectin-based artificial antibodies discussed earlier. Antibody mimics such as these, which may advantageously have a decreased ability to stimulate an immune response, may be used in combination with the present systems to effectively to provide a therapeutically effective dosage(s) of the agent directly to a region of the eye to treat, prevent, and/or reduce one or more symptoms of one or more undesirable ocular conditions. Such an antibody mimic may, for example, be directed towards a ligand such as VEGF or a VEGFR receptor in a manner that causes binding of the antibody mimic and resultant neutralization of the activity of the ligand. In the case of VEGF, the antibody mimic may inhibit or lessen the angiogenic activity of VEGF and/or a VEGFR, such as VEGFR-1, or VEGF-2.

Examples of antibody mimics, and methods for constructing antibody mimics, are provided in, for example, et al., U.S. Pat. No. 6,818,418; U.S. Pat. No. 6,951,725; U.S. Patent Application Publication 2005/0074865 and U.S. Patent Application Publication No. 2004/0259155. Compound Therapeutics, Inc. have made and described a class of certain fibronectin based "addressable" therapeutic binding molecules they term "Adnectins". Anti-VEGFR-2 Adnectin compounds include CT-322, C7S100, and C7C100, which have all shown VEGFR-2 inhibitory activity in vitro and animal models, and the first of which is schedule to enter human clinical trials in 2006. See also, e.g., Mamluk et al., J. Clin. Oncol. 23:3150 (supp. Jun. 1, 2005). In preferred embodiments the antibody mimic may be PEGylated to increase its half life and decrease enzymatic digestion of the protein.

In another preferred embodiment, the present invention comprises an intraocular drug delivery system comprising a therapeutic component comprising an anti-angiogenic and/or a neuroprotectant polypeptide component and one or more polymeric component. Even more preferably, the present invention comprises at least a portion of a naturally occurring or synthetic antibody or antibody mimic having the ability to inhibit human VEGF activity. In one embodiment the antibody portion comprises an amino acid sequence comprising a contiguous sequence of at least 10, or at least 15, or at least 20 or at least 25 or at least 30, or at least 40 or at least 50 amino acids contained in the variable heavy sequences of FIG. 3 selected from the group consisting of A.4.6.1, F(ab)-12, and humIII. In another embodiment the antibody portion comprises an amino acid sequence comprising a contiguous sequence of at least 10, or at least 15, or at least 20 or at least 25 or at least 30, or at least 40 or at least 50 amino acids contained in the variable light sequences of FIG. 3 selected from the group consisting of A.4.6.1, F(ab)-12, and humKI.

In one specific embodiment the therapeutic component comprises a humanized anti-VEGF antibody, or fragment thereof, including a Fab fragment.

In another specific embodiment the therapeutic component comprises a contiguous sequence of at least 10, or at least 15, or at least 20 or at least 25 or at least 30, or at least 40 or at least 50 amino acids of the recombinant humanized anti-VEGF Fab fragment rambizumab (Lucentis®). In another specific embodiment the therapeutic component comprises a contiguous sequence of at least 10, or at least 15, or at least 20 or at least 25 or at least 30, or at least 40 or at least 50 amino acids of the recombinant humanized anti-VEGF IgG1 synthetic antibody bevacizumab (Avastin®). In an other specific embodiment, the therapeutic component separately comprises at least 10, or at least 15, or at least 20 or at least 25 or at least 30, or at least 40 or at least 50 contiguous amino acids of the amino acid sequence of ramizumab, and at least 10, or at least 15, or at least 20 or at least 25 or at least 30, or at least 40 or at least 50 contiguous amino acids of bevacizumab.

In another preferred embodiment the present invention comprises an intraocular drug delivery system that results in the intraocular administration of a therapeutic component comprising an RNAi oligonucleotide (which may be double stranded) able to inhibit the translation of at least one VEGF or VEGFR mRNA species. In a particularly preferred embodiment the RNAi molecule comprises an siRNA oligonucleotide. In another preferred embodiment the siRNA is able to silence the expression of the VEGFR-2 receptor in a target cell. The antiVEGF-2 siRNA may comprise, for example, the following nucleotide sequences and their complementary oligonucleotide sequences, preferably their exact complements.

Examples of RNAi oligonucleotides directed against the VEGF-2 receptor may include siRNA Z, an siRNA therapeutic agent having silencing activity against VEGFR-1 and/or VEGFR-2, developed by SIRNA Therapeutics, Inc.

wherein iB is an inverted base, and TsT is a dithymidine dinucleotide segment linked by a phosphorothioate linkage. It is believed that each of these modifications adds to the nuclease resistance of the oligonucleotides. This and other relevant siRNA molecules are disclosed in e.g., U.S. Patent Publication 2005/0233344, which is hereby incorporated by reference herein in its entirety.

Essentially, siRNA Z is a modified short interfering RNA (siRNA) with an affinity for Vascular Endothelial Growth Factor Receptor-1 (VEGFR-1). VEGFR-1 has been located primarily on vascular endothelial cells and is stimulated by both VEGF and placental growth factor (PlGF), resulting in the growth of new blood vessels. By targeting VEGFR-1, siRNA Z can potentially down regulate activation of undesirable ocular angiogenesis influenced by VEGF and/or PlGF. General methods of making functional RNAi, and examples of specific siRNA are included in, for example, Kim et al., Am. J. Pathology 165:2177-2185 (2004); Tkaei et al., Cancer Res. 64:3365-3370 (May 15, 2004); Huh et al., Oncogene 24:790-800 (Jan. 27, 2005); WO 2003/070910; WO 2005/028649; WO 2005/044981; WO 2005/019453; WO 2005/0078097; WO 2003/070918; WO 2003/074654; WO 2001/75164; WO 2002/096927; U.S. Pat. Nos. 6,506,559; and 6,469,158.

Additionally, the present invention also includes the use of proteins and nucleic acids therapeutic agents, such as antibodies, antibody mimics, and siRNA molecules that are capable of inhibiting the activity (including the expression and translation) of PDGF (platelet-derived growth factor). siRNAs directed against PDGF mRNA are disclosed in U.S. Patent Publication No. 2005/0233344, which is hereby incorporated by reference herein in its entirety.

The state of the art in gene silencing through siRNA has progressed to the point whereby computer algorithms are able to analyze a given mRNA or cDNA sequence and determine effective siRNA sequences based upon such sequence. For example, Invitrogen Corp. offers a free Web-based tool called the BLOCK-IT™ RNAi Designer, in which a target mRNA is entered and will yield 10 high quality siRNA sequences. Each of these oligonucleotides would preferably be used together with their complementary, preferably exactly complementary sequences.

Preferably, though not exclusively, the polymeric component comprises a biodegradable polymer. The polymeric component may be understood to be a drug release sustaining component. The polymeric component may be joined to the therapeutic component covalently, or the therapeutic component may be dispersed within a matrix comprising the polymeric component.

A sustained-release intraocular drug delivery system in accordance with the present disclosure comprises a therapeutic component and a polymeric component associated with the therapeutic component to permit the therapeutic component to be released into the interior of an eye of an individual for at least about one week after the drug delivery system is placed in the eye. In certain embodiments disclosed herein, the therapeutic component can be released for at least about ninety days after placement in an eye, and may even be released for at least about one year after placement in the eye. The present drug delivery systems can provide targeted delivery of macromolecule therapeutic agents to intraocular tissues, such as the retina, while overcoming problems associated with conventional drug delivery methods, such as intraocular injection of non-sustained release compositions.

The therapeutic component of the present drug delivery systems comprises a non-neurotoxic macromolecule therapeutic agent. For example, the therapeutic component comprises a macromolecule therapeutic agent other than a Clostridial botulinum neurotoxin, as described in U.S. Patent Pub. No. 20040170665 (Donovan).

The present drug delivery systems may include one or more agents that are effective in reducing inflammation, reducing or preventing angiogenesis or neovascularization, reducing or preventing tumor growth, reducing intraocular pressure, protecting cells, such as retinal neurons, reducing excitotoxicity, reducing infection, and reducing hemorrhage. The therapeutic agent may be cytotoxic depending on the condition being treated. In addition, the therapeutic component may comprise a neurotoxic macromolecule, such as a botulinum neurotoxin, in combination with the non-neurotoxic macromolecule therapeutic agent discussed above. In addition, the therapeutic component may comprise a small chemical compound in combination with the present macromolecules. For example, a drug delivery system may include a small chemical compound, such as anecortave acetate, ketorolac tromethamine (such as Acular), gatifloxacin, ofloxacin, epinastine, and the like, in combination with a non-neurotoxin macromolecule therapeutic agent.

Definitions

For the purposes of this description, we use the following terms as defined in this section, unless the context of the word indicates a different meaning.

As used herein, an "intraocular drug delivery system" refers to a device or element that is structured, sized, or otherwise configured to be placed in an eye. The present drug delivery systems are generally biocompatible with physiological conditions of an eye and do not cause unacceptable or undesirable adverse side effects. The present drug delivery systems may be placed in an eye without disrupting vision of the eye. The present drug delivery systems may be in the form of a plurality of particles, such as microparticles, or may be in the form of implants, which are larger in size than the present particles.

As used herein, a "therapeutic component" refers to a portion of a drug delivery system comprising one or more macromolecular therapeutic agents, active ingredients, or substances used to treat a medical condition of the eye. The therapeutic component may be a discrete region of an intraocular implant, or it may be homogenously distributed throughout the implant or particles. The therapeutic agents of the therapeutic component are typically ophthalmically acceptable, and are provided in a form that does not cause adverse reactions when the implant is placed in an eye. As discussed herein, the therapeutic agents can be released from the drug delivery systems in a biologically active form. For example, the therapeutic agents may retain their three dimensional structure when released from the system into an eye.

As used herein, a "drug release-sustaining component" refers to a portion of the drug delivery system that is effective in providing a sustained release of the therapeutic agents of the systems. A drug release-sustaining component may be a biodegradable polymer matrix, or it may be a coating covering a core region of an implant that comprises a therapeutic component.

As used herein, "associated with" means mixed with, dispersed within, coupled to, covering, or surrounding.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the subretinal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the iris but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, retinal pigmented epithelium, Bruch's membrane, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "peptide", "polypeptide", and protein includes naturally occurring and non-naturally occurring L-amino acids, R-amino acids, and peptidomimetics. A peptidomimetic comprises a peptide-like molecule that is able to serve as a model for a peptide substrate upon which it is structurally based. Such peptidomimetics include chemically modified peptides, peptide-like molecules containing non-naturally occurring amino acids, and peptoids, which are peptide-like molecules resulting from oligomeric assembly of N-substituted glycines (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861), hereby incorporated by reference herein.

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,αdialkyl-glycine or α-aminocycloalkane carboxylic acid; an Nα-Cα cyclized amino acid; an Nα-methylated amino acid; a β- or γ-amino cycloalkane carboxylic acid; an α,β-unsaturated amino acid; a β,β-dimethyl or β-methyl amino acid; a β-substituted-2,3-methano amino acid; an NCδ or Cα-Cδ cyclized amino acid; or a substituted proline or another amino acid mimetic. In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein. The term "polypeptide" shall include peptidomimetics unless expressly indicated otherwise.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

An "oligonucleotide" or "nucleic acid" according to the present invention may comprise two or more naturally occurring or non-naturally occurring deoxyribonucleotides or ribonucleotides linked by a phosphodiester linkage, or by a linkage that mimics a phosphodiester linkage to a therapeutically useful degree. According to the present invention, an oligonucleotide will normally be considered to be single-stranded unless otherwise obvious from the context, and a nucleic acid may be single stranded or double stranded. Additionally, an oligonucleotide or nucleic acid may contain one or more modified nucleotide; such modification may be made in order to improve the nuclease resistance of the oligonucleotide, to improve the hybridization ability (i.e., raise the melting temperature or Tm) of the resulting oligonucleotide, to aid in the targeting or immobilization of the oligonucleotide or nucleic acid, or for some other purpose.

Such modifications may include oligonucleotide derivatives having modifications at the nitrogenous base, including replacement of the amino group at the 6 position of adenosine by hydrogen to yield purine; substitution of the 6-keto oxygen of guanosine with hydrogen to yield 2-amino purine, or with sulphur to yield 6-thioguanosine, and replacement of the 4-keto oxygen of thymidine with either sulphur or hydrogen to yield, respectively, 4-thiothymidine or 4-hydrothymidine. All these nucleotide analogues can be used as reactants for the synthesis of oligonucleotides. Other substituted bases are known in the art. See, e.g., Cook et al., International Publication No. WO 92/02258, entitled "Nuclease Resistant, Pyrimidine Modified Oligonucleotides that Detect and Modulate Gene Expression," which is incorporated by reference herein. Base-modified nucleotide derivatives can be commercially obtained for oligonucleotide synthesis.

Similarly, a number of nucleotide derivatives have been reported having modifications of the ribofuranosyl or deoxyribofuranosyl moiety. See, e.g., Cook et al., International Publication No. WO 94/19023, entitled "Cyclobutyl Antisense Oligonucleotides, Methods of Making and Use Thereof"; McGee et al., International Publication No. WO 94/02501, entitled "Novel 2'-O-Alkyl Nucleosides and Phosphoramidites Processes for the Preparation and Uses Thereof"; and Cook, International Publication No. WO 93/13121, entitled "Gapped 2'-Modified Oligonucleotides." Each of these publications is hereby incorporated by reference herein.

Most oligonucleotides comprising such modified bases have been formulated with increased cellular uptake, nuclease resistance, and/or increased substrate binding in mind. In other words, such oligonucleotides are described as therapeutic gene-modulating agents.

Nucleic acids having modified nucleotide residues exist in nature. Thus, depending on the type or source, modified bases in RNA can include methylated or dimethylated bases, deaminated bases, carboxylated bases, thiolated bases and bases having various combinations of these modifications. Additionally, 2'-O-alkylated bases are known to be present in naturally occurring nucleic acids. See e.g., Adams et al., *The Biochemistry of the Nucleic Acids* ($11^{th}$ ed 1992), hereby incorporated by reference herein.

Intraocular drug delivery systems have been developed which can release drug loads over various' time periods. These systems, which when placed into an eye of an individual, such as the vitreous of an eye, provide therapeutic levels of a macromolecule therapeutic agent for extended periods of time (e.g., for about one week or more). In certain embodiments, the macromolecule therapeutic agent is selected from the group consisting of anti-angiogenesis compounds, particularly anti-VEGF recombinant antibodies and antibody fragments such as rambizumab and bevacizumab, ocular hemorrhage treatment compounds, non-steroidal anti-inflammatory agents, growth factor (e.g. VEGF) inhibitors, growth factors, cytokines, antibodies, oligonucleotide aptamers, siRNA molecules and antibiotics. The disclosed systems are effective in treating ocular conditions, such as posterior ocular conditions, such as glaucoma, retinal neurodegeneration, and neovascularization, and generally improving or maintaining vision in an eye.

As discussed herein, the polymeric component of the present systems may comprise a biodegradable polymer. In certain embodiments, the therapeutic component is associated with the polymeric component as a plurality of biodegradable particles. Such particles are smaller than the implants disclosed herein, and may vary in shape. For example, certain embodiments of the present invention utilize substantially spherical particles. Other embodiments may utilize randomly configured particles, such as particles that have one or more flat or planar surfaces. The drug delivery system may comprise a population of such particles with a predetermined size distribution. For example, a major portion of the population may comprise particles having a desired diameter measurement.

In other embodiments, the therapeutic component is associated with the polymeric component as a biodegradable implant. In one embodiment of the present invention, an intraocular implant comprises a biodegradable polymer matrix. The biodegradable polymer matrix is one type of a drug release-sustaining component. The biodegradable intraocular implant comprises a therapeutic agent associated with the biodegradable polymer matrix. The matrix degrades at a rate effective to sustain release of an amount of the therapeutic agent for a time greater than about one week from the time in which the implant is placed in ocular region or ocular site, such as the vitreous of an eye.

In certain embodiments, the macromolecule therapeutic agent of the present drug delivery systems is selected from the group consisting of anti-bacterial agents, anti-angiogenic agents, anti-inflammatory agents, neuroprotectant agents, growth factor inhibitors, such as VEGF inhibitors, growth factors, cytokines, intraocular pressure reducing agents, ocular hemorrhage therapeutic agents, and the like. The therapeutic agent may be any anti-angiogenic macromolecule, any ocular hemorrhage treatment macromolecule, any non-steroidal anti-inflammatory macromolecule, any VEGF inhibitory macromolecule, any peptide or oligonucleotides-containing growth factor, any cytokine, or any peptide or oligonucleotide antibiotic that can be identified and/or obtained using routine chemical screening and synthesis techniques. For example, the macromolecule therapeutic agent may comprise an agent or region selected from the group consisting of peptides, proteins, antibodies, antibody fragments (such as, without limitation, Fab fragments), and nucleic acids. Some examples include hyaluronidase (ocular hemorrhage treatment compound), ranibizumab (Lucentis®), pegaptanib (Macugen), and VEGF inhibitors) inhibiting fragments thereof, bevacizumab (Avastin®) and VEGF inhibiting fragments thereof, pegaptanib (Macugen®) and VEGF inhibiting fragments thereof, rapamycin, cyclosporine and RNAi gene silencing oligonucleotides, such as anti-VEGF-2 inhibitory RNAi, siRNA Z and the RNAi oligonucleotides described elsewhere in this specification.

In certain embodiments, the therapeutic component of the present drug delivery systems comprises a short or small interfering ribonucleic acid (siRNA) or an oligonucleotide aptamer. For example, and in some preferred embodiments, the siRNA has a nucleotide sequence that is effective in inhibiting cellular production of vascular endothelial growth factor (VEGF) or VEGF receptors.

VEGF is a endothelial cell mitogen (Connolly D. T., et al., Tumor vascular permeability factor stimulates endothelial cell growth and angiogenesis. J. Clin. Invest. 84: 1470-1478 (1989)), that through binding with its receptor, VEGFR, plays an important role in the growth and maintenance of vascular endothelial cells and in the development of new blood- and lymphatic-vessels (Aiello L. P., et al., Vascular endothelial growth factor in ocular fluid of patients with diabetic retinopathy and other retinal disorders, New Engl. J. Med. 331: 1480-1487 (1994)).

Currently, the VEGF receptor family is believed to consist of three types of receptors, VEGFR-1 (Flt-1), VEGFR-2 (KDR/Flk-1) and VEGFR-3 (Flt-4), all of which belong to the receptor type tyrosine kinase superfamily (Mustonen T. et al., Endothelial receptor tyrosine kinases involved in angiogenesis, J. Cell Biol. 129: 895-898 (1995)). Among these receptors, VEGFR-1 appears to bind the strongest to VEGF, VEGFR-2 appears to bind more weakly than VEGFR-1, and VEGFR-3 shows essentially no binding, although it does bind to other members of the VEGF family. The tyrosine kinase domain of VEGFR-1, although much weaker than that of VEGFR-2, tranduces signals for endothelial cells. Thus, VEGF is a substance that stimulates the growth of new blood vessels. The development of new blood vessels, neovascularization or angiogenesis, in the eye is believed to cause loss of vision in wet macular degeneration and other ocular conditions, including edema.

Sustained release drug delivery systems which include active siRNA molecules can release effective amounts of active siRNA molecules that associate with a ribonuclease complex (RISC) in target cells to inhibit the production of a target protein, such as VEGF or VEGF receptors. The siRNA of the present systems can be double-stranded or single stranded RNA molecules and may have a length less than about 50 nucleotides. In certain embodiments, the systems may comprise a siRNA having a hairpin structure, and thus may be understood to be a short hairpin RNA (siRNA), as available from InvivoGen (San Diego, Calif.).

Some siRNAs that are used in the present systems preferably inhibit production of VEGF or VEGF receptors compared to other cellular proteins. In certain embodiments, the siRNAs can inhibit production of VEGF or VEGFR by at least 50%, preferably by at least 60%, and more preferably by about 70% or more. Thus, these siRNAs have nucleotide sequences that are effective in providing these desired ranges of inhibition.

The nucleotide sequence of the human VEGF isoform, VEGF 165. The nucleotide sequence has a GenBank Accession Number AB021221.

The nucleotide sequence of human VEGFR2 has a GenBank Accession Number AF063658.

One specific example of a useful siRNA is available from Acuity Pharmaceuticals (Pennsylvania) or Avecia Biotechnology under the name Cand5. Cand5 is a therapeutic agent that essentially silences the genes that produce VEGF. Thus, drug delivery systems including an siRNA selective for VEGF can prevent or reduce VEGF production in a patient in need thereof. The nucleotide sequence of Cand5 is as follows.

As mentioned above, another example of a useful siRNA is available from Sirna Therapeutics (Colorado) under the name siRNA Z. siRNA Z is a chemically modified short interfering RNA (siRNA) that targets vascular endothelial growth factor receptor-1 (VEGFR-1). Some additional examples of nucleic acid molecules that modulate the synthesis, expression and/or stability of an mRNA encoding one or more receptors of vascular endothelial growth factor are disclosed in U.S. Pat. No. 6,818,447 (Pavco).

Thus, the present drug delivery systems may comprise a VEGF or VEGFR inhibitor that includes an siRNA having a nucleotide sequence that is substantially identical to the nucleotide sequence of Cand5 or siRNA Z, identified above. For example, the nucleotide sequence of a siRNA may have at least about 80% sequence homology to the nucleotide sequence of Cand5 or siRNA Z siRNAs. Preferably, a siRNA of the present invention has a nucleotide sequence homology of at least about 90%, and more preferably at least about 95% of the Cand5 or siRNA Z siRNAs. In other embodiments, the siRNA may have a homology to a VEGF mRNA or VEGFR mRNA isoform(s) that results in the inhibition or reduction of VEGF or VEGFR synthesis in the target tissue. Examples of anti-VEGFR oligonucleotides include those described in this specification.

In another embodiment of the present drug delivery systems, the therapeutic component comprises an anti-angiogenic protein selected from the group consisting of endostatin, angiostatin, tumstatin, pigment epithelium derived factor, and VEGF TRAP (Regeneron Pharmaceuticals, New York). VEGF Trap is a fusion protein that contains portions of the extracellular domains of two different VEGF receptors connected to the Fc region (C-terminus) of a human antibody. Preparation of VEGF Trap is described in U.S. Pat. No. 5,844,099.

Other embodiments of the present systems may comprise an antibody selected from the group consisting of anti-VEGF antibodies, anti-VEGF receptor antibodies, anti-integrin antibodies, therapeutically effective fragments thereof, and combinations thereof.

Antibodies useful in the present systems include antibody fragments, such as Fab', F(ab)$_2$, Fabc, and Fv fragments. The antibody fragments may either be produced by the modification of whole antibodies or those synthesized de novo using recombinant DNA methodologies, and further include "humanized" antibodies made by now conventional techniques.

An antibody "specifically binds to" or "is immunoreactive with" a protein when the antibody functions in a binding reaction with the protein. The binding of the antibody to the protein may provide interference between the protein and its ligand or receptor, and thus the function mediated by a protein/receptor interaction can be inhibited or reduced. Several methods for determining whether or not a protein or peptide is immunoreactive with an antibody are known in the art. Immuno chemiluminescence metric assays (ICMA), enzyme-linked immunosorbent assays (ELISA) and radioimmunoassays (RIA) are some examples.

In certain specific embodiments, the present drug delivery systems comprise a monoclonal antibody that interacts with (e.g., binds to and lessens or inhibits the activity of) VEGF. Monoclonal antibodies useful in the present drug delivery systems can be obtained using routine methods known to persons of ordinary skill in the art. Briefly, animals, such as mice, are injected with a desired target protein or portion thereof, such as VEGF or VEGFR. The target protein is preferably coupled to a carrier protein. The animals are boosted with one or more target protein injections, and are hyperimmunized by an intravenous (IV) booster 3 days before fusion. Spleen cells from the mice are isolated and are fused by standard methods to myeloma cells. Hybridomas can be selected in standard hypoxanthine/aminopterin/thymine (HAT) medium, according to standard methods. Hybridomas secreting antibodies which recognize the target protein are identified, cultured, and subcloned using standard immunological techniques. In certain embodiments of the present systems, an anti-VEGF or anti-VEGFR monoclonal antibody is obtained from ImClone Systems, Inc. (NY, N.Y.). For example, the present systems may include an antibody available from ImClone Systems under the name IMC-18F1, or an antibody under the name of IMC-1121 Fab. Another anti-VEGF antibody fragment that may be used in the present drug delivery systems is produced by Genentech and Novartis under the tradename Lucentis® (ranibizumab). Lucentis® is a derivative of the Genentech anti-VEGF antibody bevacizumab, approved to treatment of colorectal cancer and marketed as Avastin®.

The present systems may also comprise an oligonucleotide aptamer that binds the 165-amino acid form of VEGF (VEGF 165). One example of a useful anti-VEGF aptamer is being produced by Eyetech Pharmaceuticals and Pfizer under the tradename Macugen® (pegaptanib sodium). Macugen® is marketed as an injectable liquid; however, in addition to having a longer lasting activity when administered by means of an implant, Macugen® may be superior in its therapeutic activity against retinal disorders when delivered in this form, as compared to administration of the liquid formulation. Aptomers may also be formulated that have an inhibitory effect against the VEGFR, such as VEGFR-2.

Another class of therapeutic agents useful in the present invention comprise VEGFR inhibitory antibody mimics, such as the VEGFR-2 inhibitors CT322, C7S100 and C7C100 made by Compound Therapeutics, Inc. These antibody mimics comprise artificial antibodies built using a fibronectin scaffold also with an "addressable" region that selectively binds a given ligand in a manner similar to the variable region of an antibody. These artificial antibodies have the added advantage of being capable to being designed to be less immunogenic than antibodies.

In addition or alternatively, the present systems may comprise a peptide that inhibits a urokinase. For example, the peptide may have 8 amino acids and is effective in inhibiting the urokinase plasminogen activator, uPA. Urokinase plasminogen activator is often observed to be overexpressed in many types of human cancer. Thus, the present systems which comprise a urokinase inhibitor can effectively treat cancer and metastasis, as well as reduce tumor growth, such as ocular tumor growth. One example of a urokinase peptide inhibitor is known as A6, which is derived from a nonreceptor binding region of uPA and includes amino acids 136-143 of uPA.

Certain of the present systems can include a combination of A6 and cisplatin and effectively reduce neovascularization in the eye. Additional peptides may have similar amino acid sequences such that the peptides have a similar inhibiting activity as A6. For example, the peptides may have conservative amino acid substitutions. Peptides that have at least 80% homology, and preferably at least about 90% homology to A6 may provide the desired inhibition of uPA.3157

The present systems may also comprise rapamycin (sirolimus). Rapamycin is a peptide that functions as an antibiotic, an immunosuppressive agent, and an anti-angiogenic agent. Rapamycin can be obtained from A.G. Scientific, Inc. (San Diego, Calif.). We have found that synergistic effects can be achieved upon use of a rapmycin intraocular implant. Rapamycin may be understood to be an immunosuppressive agent, an anti-angiogenic agent, a cytotoxic agent, or combinations thereof. The chemical formula of rapamycin is $C_{51}H_{79}NO_{13}$ and it has a molecular weight of 914.18. Rapamycin has been assigned the CAS Registry Number 53123-88-9. Rapamycin-containing drug delivery systems may provide effective treatment of one or more ocular conditions by interfering with a T-cell mediated immune response, and/or causing apoptosis in certain cell populations of the eye. Thus, rapamycin-containing drug delivery systems can provide effective treatment of one or more ocular conditions, such as uveitis, macular degeneration including age related macular degeneration, and other posterior ocular conditions. It has been discovered that by incorporating a peptide, such as rapamycin, into the present systems, therapeutically effective amounts of rapamycin can be provided in the interior of an eye with reduced side effects that may be associated with other forms of delivery, including intravitreal injection of liquid formulations and transcleral delivery. For example, the present systems may have one or more reduced side effects, such as a reduction in one or more of the following: raised lipid and cholesterol levels, hypertension, anaemia, diarrhea, rash, acne, thrombocytopenia, and decreases in platelets and haemoglobin. Although these side effects may be commonly observed upon systemic administration of rapamycin, one or more of these side effects can be observed upon ocular administration as well. U.S. Patent Publication No. 2005/0064010 (Cooper et al.) discloses transcleral delivery of therapeutic agents to ocular tissues.

In addition, rapamycin-containing implants can also be in combination with other anti-inflammatory agents, including steroidal and non-steroidal anti-inflammatory agents, other anti-angiogenic agents, and other immunosuppressive agents. Such combination therapies can be achieved by providing more than one type of therapeutic agent in the present drug delivery systems, by administering two or more drug delivery systems containing two or more types of therapeutic agents, or by administering a rapamycin-containing drug delivery system with a liquid containing ophthalmic composition containing one or more other therapeutic agents. One combination therapy approach can include placement of a drug delivery system in accordance with the disclosure herein that comprises rapamycin and dexamethasone into the vitreous of an eye. A second combination therapy approach can include placement of a drug delivery system that comprises rapamycin and cyclosporine in the vitreous of an eye. A third combination therapy approach can include placement of a drug delivery system that comprises rapamycin and triamcinolone acetonide in the vitreous of an eye. Other approaches can include placement of drug delivery systems that comprise rapamycin and tacrolimus, rapamycin and methotrexate, and other anti-inflammatory agents. In addition to the foregoing, the present drug delivery systems can include other limus compounds, such as cyclophins and FK506-binding proteins, everolimus, pimecrolimus, CCI-779 (Wyeth), AP23841 (Ariad), and ABT-578 (Abbott Laboratories). Additional limus compound analogs and derivatives useful in the present implants include those described in U.S. Pat. Nos. 5,527,907; 6,376,517; and 6,329,386; and U.S. Publication No. 20020123505.

Examples of antibiotics useful in the present macromolecule-containing drug delivery systems include cyclosporine, gatifloxacin, ofloxacin, and epinastine, and combinations thereof. Additional active ingredients that may be provided in the present systems include anecortave, hyaluronic acid, a hyaluronidase, ketorolac tromethamine, ranibizumab, bevacizumab, pegaptanib, and active fragments, derivatives, or combinations thereof.

These drug delivery systems may also include salts of the therapeutic agents when appropriate. Pharmaceutically acceptable acid addition salts are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

As discussed herein, the polymeric component of the present drug delivery systems can comprise a polymer selected from the group consisting of biodegradable polymers, non-biodegradable polymers, biodegradable copolymers, non-biodegradable copolymers, and combinations thereof. In certain preferred embodiments, the polymer is selected from the group consisting of poly-lactic acid (PLA), poly-glycolic acid (PGA), poly-lactide-co-glycolide (PLGA), polyesters, poly (ortho ester), poly(phosphazine), poly (phosphate ester), polycaprolactones, gelatin, collagen, derivatives thereof, and combinations thereof.

The present drug delivery systems may be in the form of a solid element, a semisolid element, or a viscoelastic element, or combinations thereof. For example, the present systems may comprise one or more solid, semisolid, and/or viscoelastic implants or microparticles.

The therapeutic agent may be in a particulate or powder form and entrapped by a biodegradable polymer matrix. Usually, therapeutic agent particles in intraocular implants will have an effective average size less than about 3000 nanometers. However, in other embodiments, the particles may have an average maximum size greater than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers. In addition, when such particles are combined with a polymeric component, the resulting polymeric intraocular particles may be used to provide a desired therapeutic effect.

The therapeutic agent of the present systems is preferably from about 1% to 90% by weight of the drug delivery system. More preferably, the therapeutic agent is from about 5% to about 15% by weight of the system. In a preferred embodiment, the therapeutic agent comprises about 10% by weight of the system. In another embodiment, the therapeutic agent comprises about 20% by weight of the system.

Suitable polymeric materials or compositions for use in the implant include those materials which are compatible, that is biocompatible, with the eye so as to cause no substantial interference with the functioning or physiology of the eye. Such materials preferably include polymers that are at least partially and more preferably substantially completely biodegradable or bioerodible.

In addition to the foregoing, examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Also important to controlling the biodegradation of the polymer and hence the extended release profile of the drug delivery systems is the relative average molecular weight of the polymeric composition employed in the present systems. Different molecular weights of the same or different polymeric compositions may be included in the systems to modulate the release profile. In certain systems, the relative average molecular weight of the polymer will range from about 9 to about 64 kD, usually from about 10 to about 54 kD, and more usually from about 12 to about 45 kD.

In some drug delivery systems, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the system, where a more flexible system or implant is desirable for larger geometries. The % of polylactic acid in the polylactic acid polyglycolic acid (PLGA) copolymer can be 0-100%, preferably about 15-85%, more preferably about 35-65%. In some systems, a 50/50 PLGA copolymer is used.

The biodegradable polymer matrix of the present systems may comprise a mixture of two or more biodegradable polymers. For example, the system may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. It may be understood that the polymeric component of the present systems is associated with the therapeutic component so that the release of the therapeutic component into the eye is by one or more of diffusion, erosion, dissolution, and osmosis. As discussed herein, the matrix of an intraocular drug delivery system may release drug at a rate effective to sustain release of an amount of the therapeutic agent for more than one week after implantation into an eye. In certain systems, therapeutic amounts of the therapeutic agent are released for more than about one month, and even for about twelve months or more. For example, the therapeutic component can be released into the eye for a time period from about ninety days to about one year after the system is placed in the interior of an eye.

The release of the therapeutic agent from the intraocular systems comprising a biodegradable polymer matrix may include an initial burst of release followed by a gradual increase in the amount of the therapeutic agent released, or the release may include an initial delay in release of the therapeutic agent followed by an increase in release. When the system is substantially completely degraded, the percent of the therapeutic agent that has been released is about one hundred. Compared to existing implants, the systems disclosed herein do not completely release, or release about 100% of the therapeutic agent, until after about one week of being placed in an eye.

It may be desirable to provide a relatively constant rate of release of the therapeutic agent from the drug delivery system over the life of the system. For example, it may be desirable for the therapeutic agent to be released in amounts from about 0.01 μg to about 2 μg per day for the life of the system. However, the release rate may change to either increase or decrease depending on the formulation of the biodegradable polymer matrix. In addition, the release profile of the therapeutic agent may include one or more linear portions and/or one or more non-linear portions. Preferably, the release rate is greater than zero once the system has begun to degrade or erode wherein the system is formulated to release at least 10%, 20%, 30%, or 40% of its active ingredient in the first two weeks following administration to the posterior chamber of a human eye.

As discussed in the examples herein, the present drug delivery systems comprise a therapeutic component and a polymeric component, as discussed above, which are associated to release an amount of the macromolecule therapeutic agent that is effective in providing a concentration of the macromolecule therapeutic agent in the vitreous of the eye in a range from about 0.2 nM to about 5 μM. In addition or alternatively, the present systems can release a therapeutically effective amount of the macromolecule at a rate from about 0.003 μg/day to about 5000 μg/day. As understood by persons of ordinary skill in the art, the desired release rate and target drug concentration will vary depending on the particular therapeutic agent chosen for the drug delivery system, the ocular condition being treated, and the patient's health. Optimization of the desired target drug concentration and release rate can be determined using routine methods known to persons of ordinary skill in the art.

The drug delivery systems, such as the intraocular implants, may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including the therapeutic agent(s) described herein, may be distributed in a non-homogenous pattern in the matrix. For example, the drug delivery system may include a portion that has a greater concentration of the therapeutic agent relative to a second portion of the system. The present drug delivery systems may be in the form of solid implants, semisolid implants, and viscoelastic implants, as discussed herein.

The intraocular implants disclosed herein may have a size of between about 5 μm and about 2 mm, or between about 10 μm and about 1 mm for administration with a needle, greater than 1 mm, or greater than 2 mm, such as 3 mm or up to 10 mm, for administration by surgical implantation. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 μg, more preferably about 500-1000 μg. For example, an implant may be about 500 μg, or about 1000 μg. However, larger implants may also be formed and further processed before administration to an eye. In addition, larger implants may be desirable where relatively greater amounts of a therapeutic agent are provided in the implant, as discussed in the examples herein. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Drug delivery systems can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The drug delivery systems may be of any geometry including fibers, sheets, films, microspheres, spheres, circular discs, plaques and the like. The upper limit for the system size will be determined by factors such as toleration for the system, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 μm to 4 mm in diameter, with comparable volumes for other shaped particles.

The size and form of the system can also be used to control the rate of release, period of treatment, and drug concentration at the site of implantation. For example, larger implants will deliver a proportionately larger dose, but depending on the surface to mass ratio, may have a slower release rate. The particular size and geometry of the system are chosen to suit the site of implantation.

The proportions of therapeutic agent, polymer, and any other modifiers may be empirically determined by formulating several implants, for example, with varying proportions of such ingredients. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the therapeutic agent included in the intraocular drug delivery systems disclosed hereinabove, the systems may also include one or more additional ophthalmically acceptable therapeutic agents. For example, a system may include one or more antihistamines, one or more different antibiotics, one or more beta blockers, one or more steroids, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. Nos. 4,474,451, columns 4-6 and 4,327,725, columns 7-8.

Examples of antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, cyclosporine, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, gatifloxacin, ofloxacin, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, fluorometholone, dexamethasone, medrysone, loteprednol, fluazacort, hydrocortisone, prednisone, betamethasone, prednisone, methylprednisolone, riamcinolone hexacatonide, paramethasone acetate, diflorasone, fluocinonide, fluocinolone, triamcinolone, triamcinolone acetonide, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valciclovir, dideoxycytidine, phosphonoformic acid, ganciclovir and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, prostaglandins, antiparasitics, antifungals, and derivatives thereof. A suitable carbonic anhydrase inhibitor can be a compound such as acetazolamide, brinzolamide, dorzolamide, methazolamide, and certain thiophene sulfonamides.

The amount of active agent or agents employed in the drug delivery system, individually or in combination, will vary widely depending on the effective dosage required and the desired rate of release from the system. As indicated herein, the agent will be at least about 1, more usually at least about 10 weight percent of the system, and usually not more than about 80.

In addition to the therapeutic component, the intraocular drug delivery systems disclosed herein may include an excipient component, such as effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9 and more preferably about 4 to about 8. As such the buffering agent may be as much as about 5% by weight of the total system. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

In addition, the drug delivery systems may include a solubility enhancing component provided in an amount effective to enhance the solubility of the therapeutic agent relative to substantially identical systems without the solubility enhancing component. For example, an implant may include a β-cyclodextrin, which is effective in enhancing the solubility of the therapeutic agent. The β-cyclodextrin may be provided in an amount from about 0.5% (w/w) to about 25% (w/w) of the implant. In certain implants, the β-cyclodextrin is provided in an amount from about 5% (w/w) to about 15% (w/w) of the implant. Other implants may include a gamma-cyclodextrin, and/or cyclodextrin derivatives.

Lipid nanoparticles can also be used as a carrier for the therapeutic agent (i.e. a siRNA). See eg published U.S. patent application 2006 0024374 A1; Wissing S. A., et al, *Solid lipid nanoparticles for parenteral drug delivery*, Adv Drug Del Rev 56 (2004), 1257-1272; Schwarz C., et al., *Freeze-drying of drug free and drug loaded solid lipid nanoparticles (SLN)*, Int J Pharm 157 (1997), 171-179.

In some situations mixtures of drug delivery systems may be utilized employing the same or different pharmacological agents. In this way, a cocktail of release profiles, giving a biphasic or triphasic release with a single administration is achieved, where the pattern of release may be greatly varied. As one example, a mixture may comprise a plurality of polymeric microparticles and one or more implants.

Additionally, release modulators such as those described in U.S. Pat. No. 5,869,079 may be included in the drug delivery systems. The amount of release modulator employed will be dependent on the desired release profile, the activity of the modulator, and on the release profile of the therapeutic agent in the absence of modulator. Electrolytes such as sodium chloride and potassium chloride may also be included in the systems. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

Thus, in one embodiment, an intravitreal drug delivery system comprises a biodegradable polymer component, such as PLGA, and rapamycin. The system can be in the form of a biodegradable intravitreal implant, or a population of biodegradable polymeric microparticles. The drug delivery system includes an amount of rapamycin that when released from the system, the rapamcycin can provide a therapeutic effect. For example, a drug delivery system can comprise an amount of rapamycin from about 50 micrograms to about 1000 micrograms. In certain preferred embodiments, a 1 milligram biodegradable implant comprises an amount of rapamycin from about 500 micrograms to about 600 micrograms. These biodegradable intravitreal drug delivery systems release therapeutically effective amounts of rapamycin for prolonged periods of time relative to intravitreal injections of liquid containing rapamycin formulations or other delivery techniques. The prolonged delivery of therapeutically effective amounts can provide improved clinical outcomes not observed with other rapamycin ocular therapies. Rapamycin can be released in therapeutically effective amounts for one month or more. In certain embodiments, therapeutically effective amounts of rapamycin are released from the implants for at least about three months, and can provide therapeutic benefits that last for at least about one year or more. For example, the rapamycin can be released from the implant at a rate from about 0.1 micrograms/day to about 200 micrograms/day. Such release rates may be appropriate to provide rapamycin concentrations from about 1 nanogram/ml to about 50 ng/ml. The rapamycin-containing implant can be placed in the vitreous of an eye to treat macular degeneration, including without limitation age related macular degeneration, uveitis, ocular tumors, neovascularization, including choroidal neovascularization, and the like.

In another embodiment, an intravitreal drug delivery system comprises a biodegradable polymer, such as PLGA, and a VEGF/VEGFR inhibitor. (particularly rambizumab or bevacizumab or VEGF-inhibiting derivatives or fragments of either of these). The system can be in the form of a biodegradable intravitreal implant, or a population of biodegradable polymeric microparticles. The drug delivery system includes an amount of a VEGF/VEGFR inhibitor that when released from the system, the inhibitor can provide a therapeutic effect. For example, the biodegradable implant can comprise a peptide, a nucleic acid molecule, a protein, or other agent that interferes with interactions between VEGF and VEGFR. Examples of useful inhibitors are described above. These drug delivery systems provide prolonged delivery of the VEGF inhibitor directly into the vitreous of an eye in need of treatment. Thus, these drug delivery systems can provide effective treatment of one or more ocular conditions, including without limitation, neovascularization, ocular tumors, and the like.

Embodiments of the present invention also relate to compositions comprising the present drug delivery systems. For example, and in one embodiment, a composition may comprise the present drug delivery system and an ophthalmically acceptable carrier component. Such a carrier component may be an aqueous composition, for example saline or a phosphate buffered liquid.

The present drug delivery systems are preferably administered to patients in a sterile form. For example, the present drug delivery systems, or compositions containing such systems, may be sterile when stored. Any routine suitable method of sterilization may be employed to sterilize the drug delivery systems. For example, the present systems may be sterilized using radiation. Preferably, the sterilization method does not reduce the activity or biological or therapeutic activity of the therapeutic agents of the present systems.

The drug delivery systems can be sterilized by gamma irradiation. As an example, the implants can be sterilized by 2.5 to 4.0 mrad of gamma irradiation. The implants can be terminally sterilized in their final primary packaging system including administration device e.g. syringe applicator. Alternatively, the implants can be sterilized alone and then aseptically packaged into an applicator system. In this case the applicator system can be sterilized by gamma irradiation, ethylene oxide (ETO), heat or other means. The drug delivery systems can be sterilized by gamma irradiation at low temperatures to improve stability or blanketed with argon, nitrogen or other means to remove oxygen. Beta irradiation or e-beam may also be used to sterilize the implants as well as UV irradiation. The dose of irradiation from any source can be lowered depending on the initial bioburden of the implants such that it may be much less than 2.5 to 4.0 mrad. The drug delivery systems may be manufactured under aseptic conditions from sterile starting components. The starting components may be sterilized by heat, irradiation (gamma, beta, UV), ETO or sterile filtration. Semi-solid polymers or solutions of polymers may be sterilized prior to drug delivery system fabrication and macromolecule incorporation by sterile filtration of heat. The sterilized polymers can then be used to aseptically produce sterile drug delivery systems.

Various techniques may be employed to produce the drug delivery systems described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the drug delivery systems, and typically yield elements with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

In certain embodiments of the present invention, a method of producing a sustained-release intraocular drug delivery system, comprises combining a non-neurotoxic macromolecule therapeutic agent and a polymeric material to form a drug delivery system suitable for placement in the interior of an eye of an individual. The resulting drug delivery system is effective in releasing the macromolecule therapeutic agent into the eye for at least about one week after the drug delivery system is placed in the eye. The method may comprise a step of extruding a particulate mixture of the macromolecule therapeutic agent and the polymeric material to form an extruded composition, such as a filament, sheet, and the like. The macromolecule preferably retains its biological activity when the macromolecule is released from the drug delivery system. For example, the macromolecule may be released having a structure that is identical or substantially identical to the native structure of the macromolecule under physiological conditions.

When polymeric particles are desired, the method may comprise forming the extruded composition into a population of polymeric particles or a population of implants, as described herein. Such methods may include one or more steps of cutting the extruded composition, milling the extruded composition, and the like.

As discussed herein, the polymeric material may comprise a biodegradable polymer, a non-biodegradable polymer, or a combination thereof. Examples of polymers and macromolecule therapeutic agents include each and every one of the polymers and agents identified above.

As discussed herein, the present systems may be configured to release the macromolecule therapeutic agent into the eye at a rate from about 0.003 µg/day to about 5000 µg/day. Thus, the foregoing methods may combine the polymeric component and the therapeutic component to form a drug delivery system with such desirable release rates. In addition, the present systems can be configured to provide amounts of the macromolecule therapeutic agent that are cleared from the vitreous at a desired target rate. As described in the examples, the clearance rates can range from about 3 mL/day to about 15 mL/day. However, certain implants can release therapeutically effective amounts of the macromolecule therapeutic agent that are cleared from the vitreous at lower rates, such as less than about 1 mL/day. For example, Gaudreault et al. ("Preclinical pharmacokinetics of ranibizumab (rhuFabV2) after a single intravitreal administration", IOVS, (2005); 46(2):726-733) reports that ranibizumab can be cleared from the vitreous at rates of about 0.5 to about 0.7 mL/day when a ranibuzmab formulation is intravitreally injected.

As described herein, it has been discovered that the present systems can be formed by extruding a polymeric component/therapeutic component mixture without disrupting the biological activity of the macromolecule therapeutic agent. For example, implants have been invented which include a macromolecule that retains its structure after an extrusion process. Thus, in spite of the manufacturing conditions, drug delivery systems in accordance with the disclosure herein have been invented which include biologically active macromolecules.

The drug delivery systems of the present invention may be inserted into the eye, for example the vitreous chamber of the eye, by a variety of methods, including intravitreal injection or surgical implantation. For example, the drug delivery systems may be placed in the eye using forceps or a trocar after making a 2-3 mm incision in the sclera. Preferably, the present systems can be placed in an eye without making an incision. For example, the present systems may be placed in an eye by inserting a trocar or other delivery device directly through the eye without an incision. The removal of the device after the placement of the system in the eye can result in a self-sealing opening. One example of a device that may be used to insert the implants into an eye is disclosed in U.S. Patent Publication No. 2004/0054374. The method of placement may influence the therapeutic component or drug release kinetics. For example, delivering the system with a trocar may result in placement of the system deeper within the vitreous than placement by forceps, which may result in the system being closer to the edge of the vitreous. The location of the system may influence the concentration gradients of therapeutic component or drug surrounding the element, and thus influence the release rates (e.g., an element placed closer to the edge of the vitreous may result in a slower release rate).

The present systems are configured to release an amount of the therapeutic agent effective to treat or reduce a symptom of an ocular condition, such as an ocular condition such as glaucoma or edema. More specifically, the systems may be used in a method to treat or reduce one or more symptoms of glaucoma or proliferative vitreoretinopathy.

The systems disclosed herein may also be configured to release additional therapeutic agents, as described above, which to prevent diseases or conditions, such as the following:

Maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

In one embodiment, an implant is administered to a posterior segment of an eye of a human or animal patient, and preferably, a living human or animal. In at least one embodiment, an implant is administered without accessing the subretinal space of the eye. However, in other embodiments the implant may be inserted into the subretinal space. For example, a method of treating a patient may include placing the implant directly into the posterior chamber of the eye. In other embodiments, a method of treating a patient may comprise administering an implant to the patient by at least one of intravitreal placement, subretinal placement, subconjunctival placement, sub-tenon placement, retrobulbar placement, and suprachoroidal placement. Placement methods may include injection and/or surgical insertion.

In at least one embodiment, a method of reducing neovascularization or angiogenesis in a patient comprises administering one or more implants containing one or more therapeutic agents, as disclosed herein to a patient by at least one of intravitreal injection, subconjunctival injection, sub-tenon injection, retrobulbar injection, and suprachoroidal injection. A syringe apparatus including an appropriately sized needle, for example, a 22 gauge needle, a 27 gauge needle or a 30 gauge needle, can be effectively used to inject the composition with the posterior segment of an eye of a human or animal. Repeat injections are often not necessary due to the extended release of the therapeutic agent from the implants.

In another aspect of the invention, kits for treating an ocular condition of the eye are provided, comprising: a) a container comprising an extended release implant comprising a therapeutic component including a therapeutic agent as herein described, and a drug release sustaining component; and b) instructions for use. Instructions may include steps of how to handle the implants, how to insert the implants into an ocular region, and what to expect from using the implants.

EXAMPLES

The following examples are not intended to limit the scope of the invention.

Example 1

Manufacture and Testing of Implants Containing a Therapeutic Agent and a Biodegradable Polymer Matrix Biodegradable implants are made by combining a therapeutic agent, such as those agents described above, with a biodegradable polymer composition in a stainless steel mortar. The combination is mixed via a Turbula shaker set at 96 RPM for 15 minutes. The powder blend is scraped off the wall of the mortar and then remixed for an additional 15 minutes. The mixed powder blend is heated to a semi-molten state at specified temperature for a total of 30 minutes, forming a polymer/drug melt.

Rods are manufactured by pelletizing the polymer/drug melt using a 9 gauge polytetrafluoroethylene (PTFE) tubing, loading the pellet into the barrel and extruding the material at the specified core extrusion temperature into filaments. The filaments are then cut into about 1 mg size implants or drug delivery systems. The rods have dimensions of about 2 mm long×0.72 mm diameter. The rod implants weigh between about 900 µg and 1100 µg.

Wafers are formed by flattening the polymer melt with a Carver press at a specified temperature and cutting the flattened material into wafers, each weighing about 1 mg. The wafers have a diameter of about 2.5 mm and a thickness of about 0.13 mm. The wafer implants weigh between about 900 µg and 1100 µg.

In-vitro release testing can be performed on each lot of implant (rod or wafer). Each implant may be placed into a 24 mL screw cap vial with 10 mL of Phosphate Buffered Saline solution at 37° C. and 1 mL aliquots are removed and replaced with equal volume of fresh medium on day 1, 4, 7, 14, 28, and every two weeks thereafter.

Drug assays may be performed by HPLC, which consists of a Waters 2690 Separation Module (or 2696), and a Waters 2996 Photodiode Array Detector. An Ultrasphere, C-18 (2), 5 mm; 4.6×150 mm column heated at 30° C. can be used for separation and the detector can be set at 264 nm. The mobile phase can be (10:90) MeOH—buffered mobile phase with a flow rate of 1 mL/min and a total run time of 12 min per sample. The buffered mobile phase may comprise (68:0.75:0.25:31) 13 mM 1-Heptane Sulfonic Acid, sodium salt-glacial acetic acid-triethylamine-Methanol. The release rates can be determined by calculating the amount of drug being released in a given volume of medium over time in mg/day.

The polymers chosen for the implants can be obtained from Boehringer Ingelheim or Purac America, for example. Examples of polymers include: RG502, RG752, R202H, R203 and R206, and Purac PDLG (50/50). RG502 is (50:50) poly(D,L-lactide-co-glycolide), RG752 is (75:25) poly(D,L-lactide-co-glycolide), R202H is 100% poly(D, L-lactide) with acid end group or terminal acid groups, R203 and R206 are both 100% poly(D, L-lactide). Purac PDLG (50/50) is (50:50) poly(D,L-lactide-co-glycolide). The inherent viscosity of RG502, RG752, R202H, R203, R206, and Purac PDLG are 0.2, 0.2, 0.2, 0.3, 1.0, and 0.2 dL/g, respectively. The average molecular weight of RG502, RG752, R202H, R203, R206, and Purac PDLG are, 11700, 11200, 6500, 14000, 63300, and 9700 daltons, respectively.

Example 2

Treatment of an Ocular Condition with an Anti-Inflammatory Active Agent Intraocular Implant A controlled release drug delivery system can be used to treat an ocular condition. The system can contain a steroid, such an anti-inflammatory steroid, such as dexamethasone as the active agent. Alternately or in addition, the active agent can be a non-steroidal anti-inflammatory, such as ketoralac (available from Allergan, Irvine, Calif. as ketorolac tromethamine ophthalmic solution, under the tradename Acular). Thus, for example, a dexamethasone or ketorolac extended release implant system made in accordance with Example 1 can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using the procedure (trocar implantation) described herein. The implant(s) can release a therapeutic amount of, for example the dexamethazone or the ketorolac for an extended period of time to thereby treat a symptom of the ocular condition, such as for at least about one week from the time of implantation, and up to several months, such as about 6 months or more.

Example 3

Preparation and Therapeutic Use of an Anti-Angiogenesis Extended Release Implant(s)

An implant to treat an ocular condition according to the present invention can contain a steroid, such an anti-angiogenesis steroid, such as an anecortave, as the active agent. Thus, a bioerodible implant system for extended delivery of anecortave acetate (an angiostatic steroid) can be made using the method of Example 1. The implant or implants can be loaded with a total of about 15 mg of the anecortave.

The anecortave acetate extended release implant system can be implanted into an ocular region or site (i.e. into the vitreous) of a patient with an ocular condition for a desired therapeutic effect. The ocular condition can be an angiogenic condition or an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. The implant(s) can be inserted into the vitreous using the procedure (trocar implantation) described herein. The implant(s) can release a therapeutic amount of the anecortave for an extended period of time to thereby treat a symptom of the ocular condition.

Example 4

Preparation and Therapeutic Use of an Anti-VEGF Extended Release Implant(s)

VEGF (Vascular Endothelial Growth Factor) (also known as VEGF-A) is a growth factor which can stimulate vascular endothelial cell growth, survival, and proliferation. VEGF is believed to play a central role in the development of new blood vessels (angiogenesis) and the survival of immature blood vessels (vascular maintenance). Tumor expression of VEGF can lead to the development and maintenance of a vascular network, which promotes tumor growth and metastasis. Thus, increased VEGF expression correlates with poor prognosis in many tumor types. Inhibition of VEGF can be an anticancer therapy used alone or to complement current therapeutic modalities (eg, radiation, chemotherapy, targeted biologic therapies).

VEGF is believed to exert its effects by binding to and activating two structurally related membrane receptor tyrosine kinases, VEGF receptor-1 (VEGFR-1 or flt-1) and VEGFR-2 (flk-1 or KDR), which are expressed by endothelial cells within the blood vessel wall. VEGF may also interact with the structurally distinct receptor neuropilin-1. Binding of VEGF to these receptors initiates a signaling cascade, resulting in effects on gene expression and cell survival, proliferation, and migration. VEGF is a member of a family of structurally related proteins (see Table A below). These proteins bind to a family of VEGFRs (VEGF receptors), thereby stimulating various biologic processes. Placental growth factor (PlGF) and VEGF-B bind primarily to VEGFR-1. PlGF modulates angiogenesis and may also play a role in the inflammatory response. VEGF-C and VEGF-D bind primarily to VEGFR-3 and stimulate lymphangiogenesis rather than angiogenesis.

TABLE A

| VEGF Family Members | Receptors | Functions |
|---|---|---|
| VEGF (VEGF-A) | VEGFR-1, VEGFR-2, neuropilin-1 | Angiogenesis Vascular maintenance |
| VEGF-B | VEGFR-1 | Not established |
| VEGF-C | VEGF-R, VEGFR-3 | Lymphangiogenesis |
| VEGF-D | VEGFR-2, VEGFR-3 | Lymphangiogenesis |
| VEGF-E (viral factor) | VEGFR-2 | Angiogenesis |
| PlGF | VEGFR-1, neuropilin-1 | Angiogenesis and inflammation |

An extended release bioerodible implant system can be used to treat an ocular condition mediated by a VEGF. Thus, the implant can contain as active agent a VEGF inhibitor. For example, either ranibizumab (Lucentis®; rhuFab V2) (or bevacizumab (Avastin®; rhuMab-VEGF), both made by Genentech, South San Francisco, Calif.), and the implant(s) an be made using the method of Example 1. Ranibizumab and bevacizumab are both anti-VEGF (vascular endothelial growth factor) antibody products that may have particular utility for patients with macular degeneration, including the wet form of age-related macular degeneration. The implant or implants can be loaded with a total of about 50 to about 500 μg or more of the ranibizumab (i.e. about 150 μg of ranibizumab can be loaded into the implants prepared according to the Example 1 method). Bevacizumab is approved as an antiangiogenic for the treatment of colorectal cancer at a concentration of 1 mg/ml. However, it is currently being divided by pharmacists into small portions (approximately 50 μl to approximately 100 μl in volume) for intravitreal injection. The use of Avastin® for age-related macular degeneration would benefit from inclusion into a extended release implant system in accordance with the present invention. In addition, one or more implant device may be injected into the eye to deliver a higher amount of the drug than would otherwise be given. Ranibizumab is a humanized Fab, and a derivative of the humanized anti-VEGF synthetic IgG1 bevacizumab. It will be understood that with regard to its inclusion into an implant or drug delivery system according top the present invention, reference to ranibizumab in the examples of this specification is substantially equally applicable to, and shall constitute a disclosure of the use in the same manner of, bevacizumab.

The ranibizumab (or bevacizumab) extended release implant system or systems can be implanted into an ocular region or site (i.e. into the vitreous) of a patient with an ocular condition for a desired therapeutic effect. The ocular condition can be an inflammatory condition such as uveitis or the patient can be afflicted with one or more of the following afflictions: macular degeneration (including non-exudative age related macular degeneration and exudative age related macular degeneration); choroidal neovascularization; acute macular neuroretinopathy; macular edema (including cystoid macular edema and diabetic macular edema); Behcet's disease, diabetic retinopathy (including proliferative diabetic retinopathy); retinal arterial occlusive disease; central retinal vein occlusion; uveitic retinal disease; retinal detachment; retinopathy; an epiretinal membrane disorder; branch retinal vein occlusion; anterior ischemic optic neuropathy; non-retinopathy diabetic retinal dysfunction, retinitis pigmentosa and glaucoma. In a preferred embodiment, the condition comprises age related macular degeneration. The implant(s) can be inserted into the vitreous using the procedure (trocar implantation) as described herein, or by incision. The implant(s) can release a therapeutic amount of the ranibizumab for an extended period of time, such as for one 1 month, or 2 months, or 3 months, or 4 months or 5 months or more, or even more than six months, to thereby treat a symptom of the ocular condition.

Pegaptanib is an aptamer that can selectively bind to and neutralize VEGF and may have utility for treatment of, for example, age-related macular degeneration and diabetic macular edema by inhibiting abnormal blood vessel growth and by stabilizing or reverse blood vessel leakage in the back of the eye resulting in improved vision. A bioerodible implant system for extended delivery of pegaptanib sodium (Macugen; Pfizer Inc, New York or Eyetech Pharmaceuticals, New York) can also be made using the method of Example 1, but with use of pegaptanib sodium as the active agent. The implant or implants can be loaded with a total of about 1 mg to 3 mg of Macugen according to the Example 1 method.

The pegaptanib sodium extended release implant system can be implanted into an ocular region or site (i.e. into the vitreous) of a patient with an ocular condition for a desired therapeutic effect.

An extended release bioerodible intraocular implant for treating an ocular condition, such as an ocular tumor can also be made as set forth in Example 1, using about 1-3 mg of the VEGF Trap compound available from Regeneron, Tarrytown, N.Y.

Example 5

Pharmacokinetic Parameters of Macromolecule Therapeutic Agents

For a drug that does not cross the retinal pigmented epithelium or the retinal vessels, its vitreous clearance is governed by the rate at which it diffuses through the vitreous to the lens zonulas. Given the volume of the vitreous and the small area of the retrozonular spaces, constraining geometric factors can limit this process. Molecular weight is an important factor in the rate of vitreous clearance of an agent since the clearance is a diffusion limited process. The posterior chamber aqueous humor is exchanged at a relatively constant rate with the anterior chamber from where the aqueous humor is eliminated from the eye. Because of the constant turnover of aqueous humor when a steady state concentration gradient of the drug in the vitreous is established, both aqueous humor concentrations and vitreous concentrations will decline in a parallel exponential fashion. At this point the ratio of the aqueous humor concentration of drug and the vitreous humor concentration of drug ($C_a/C_v$) will remain constant. The rate constant of vitreous loss is related to this ratio by mass balance as defined by $k_v C_v V_v = kf V_a C_a$ where $k_v$ is the vitreous loss coefficient, $C_a$ and $C_v$ are the aqueous humor and vitreous concentrations of drug, $V_a$ and $V_v$ are the volumes of the aqueous and vitreous humors respectively, and kf is the loss coefficient of the posterior chamber aqueous humor which is equal to the ratio of the rate of aqueous humor turnover ($f_a$) and the volume of the aqueous humor. Hence, the ratio of vitreous humor concentration to aqueous humor concentration can be defined by the following relationship:

$$k_v = \frac{f_a \cdot C_a}{V_v \cdot C_v}$$

Using this relationship, the vitreous half-lives of molecules as a function of their molecular weight have been calculated and are shown in Table 1 below. Experiments with gentamicin, streptomycin, and sulfacetamide have validated this relationship. The vitreous kinetic treatment primarily applies to agents that are cleared via the anterior route and assumes an insignificant loss across the retina.

TABLE 1

Example Peptides, Proteins, siRNA, Antibodies and Their Estimated Pharmacodynamic Parameters.

| Macro-molecule | Pharmacologic Target | M.W. | | Target Concentration | Estimated Vitreous $t_{1/2}$ (days) |
|---|---|---|---|---|---|
| ranibizumab (rhu Fab V2) | anti-VEGF antibody | 48 | kD | 1-5 nM | 4.19 |
| bevacizumab (rhuMab-VEGF) | Anti-VEGF antibody | 149 | KD | 1-5 nM | 4.19 |
| Fab IMC 1121 | anti-VEGFR-2 antibody | 45 | kD | 0.7-1 nM | 4.13 |

TABLE 1-continued

Example Peptides, Proteins, siRNA, Antibodies and Their Estimated Pharmacodynamic Parameters.

| Macro-molecule | Pharmacologic Target | M.W. | | Target Concentration | Estimated Vitreous $t_{1/2}$ (days) |
|---|---|---|---|---|---|
| F200 Fab | anti- a5B1 integrin antibody | 50 | kD | 1-2 nM | 4.22 |
| endostatin | endogenous anti-angiogenic protein | 20 | kD | 1 µM | 3.49 |
| angiostatin | endogenous anti-angiogenic protein | 32 | kD | 1-5 nM | 3.86 |
| Pigment Epithelium Derived Factor (PEDF) | endogenous anti-angiogenic protein | 50 | kD | 0.5-1 nM | 4.22 |
| VEGF Trap | VEGF binding protein | 120 | kD | 0.2-1 nM | 4.91 |
| A6 | 8 a.a. peptide, uPA inhibitor | 1 | kD | 5-10 nM | 1.11 |
| Cand5 | siRNA against VEGF | 11 | kD | 1-5 µM | 3.01 |
| siRNA Z | siRNA against VEGFR-1 | 11 | kD | 1-5 µM | 3.01 |
| pegaptanib sodium (Macugen) | oligonucleotide aptamer binds VEGF165 | 40 | kD | 0.2-3 nM | 4.04 |

Based on the above estimated half-lives and required concentrations it was possible to estimate the required delivery rate for intravitreal drug delivery. At steady state in a well stirred compartment the concentration is a function of clearance and delivery rate. Specifically:

$$Css = \frac{Ro}{Cl}$$

Where Css is the steady state vitreous concentration, Ro the rate of drug release from an intravitreal implant and Cl the vitreous clearance of the compound. Assuming a volume of distribution equal to the physiologic volume of the vitreous, (V=3 mL), it is possible to estimate the Cl (Cl=V*K) from the data in Table 1. These values are presented in Table 2 along with the required delivery rate to achieve the desired target concentrations.

Considerable concentration gradients may exist within the vitreous. Additionally, the volume of distribution of an agent may be significantly higher due to melanin or protein binding. Both these factors may be expected to increase the release rate requirements to achieve a fixed desired target concentration at the macula. On the other hand, the clearance may be faster due to intraocular metabolism of the peptide or protein. The present delivery systems are capable of delivering a nominal theoretical rate of drug release as well as rates ranging from 10 fold below to 10 fold higher than the theoretical nominal.

Drug Delivery Rate Estimation

TABLE 2

Example Peptides, Proteins, siRNA, Antibodies and Their Estimated Pharmacodynamic Parameters.

| Macromolecule | Target Concentration | Estimated Vitreous $t_{1/2}$ (days) | Estimated Cl (mL/day) | Delivery Rate Range (µg/day) | Amount Range (µg) to be loaded in implant 35 days (rate * 35) | Specific amount (µg) to be loaded |
|---|---|---|---|---|---|---|
| ranibizumab (rhu Fab V2) | 1-5 nM | 4.19 | 12.57 | 0.302-30.2 | 10.6-1060 | 500 |
| bevacizumab (rhuMab-VEGF) | 1-5 nM | 4.19 | 12.57 | 0.302-30.2 | 31.8-3180 | 1500 |
| Fab IMC 1121 | 0.7-1 nM | 4.13 | 12.39 | 0.056-5.58 | 1.96-195.3 | 100 |
| F200 Fab | 1-2 nM | 4.22 | 12.66 | 0.127-12.7 | 4.4-444.5 | 200 |
| endostatin | 1 uM | 3.49 | 10.47 | 20.9-2090 | 731.5-73150 | 35000 |
| angiostatin | 1-5 nM | 3.86 | 11.58 | 0.185-18.5 | 6.5-647.5 | 350 |
| Pigment Epithelium Derived Factor (PEDF) | 0.5-1 nM | 4.22 | 12.66 | 0.063-6.33 | 2.2-221.6 | 110 |
| VEGF Trap | 0.2-1 nM | 4.91 | 14.73 | 0.177-17.7 | 6.2-619.5 | 310 |
| A6 | 5-10 nM | 1.11 | 3.33 | 0.003-0.333 | 0.11-11.7 | 5 |
| Cand5 | 1-5 uM | 3.01 | 9.03 | 49.7-4970 | 1739.5-173950 | 86100 |
| siRNA Z | 1-5 uM | 3.01 | 9.03 | 49.7-4970 | 1739.5-173950 | 86100 |
| Pegaptanib sodium (Macugen) | 0.2-3 nM | 4.04 | 12.12 | 0.145-14.5 | 5.1-507.5 | 250 |

Example 6

Biologically Active Macromolecules Sustained Release Drug Delivery Systems

A particular macromolecule, bovine serum albumin (BSA) was incorporated into poly(lactide-co-glycolide) polymer implant drug delivery systems (DDSs). BSA is a macromolecule with a relatively high water solubility. BSA denatures at elevated temperatures. Several polymer systems were used which ranged in lactide-glycolide ratios and intrinsic viscosity. The implants were made by melt extrusion at about 80° C. (50° C. to 78° C.) or less. Various BSA release profiles were obtained by loading and by milling the starting materials.

BSA was obtained from Sigma (Sigma brand albumin, bovine serum, fraction V, minimum 96% by analysis, lyophilized powder, CAS #9048-46-8). Different polymer compositions were obtained from Boehring Ingelheim Corp. Specific polymers are as follows: resomer RG502H, 50:50 Poly (D,L-lactide-co-glycolide), Boehringer Ingelheim Corp. Lot #R03F015; resomer RG752, 75:25 Poly(D,L-lactide-co-glycolide), Boehringer Ingelheim Corp. Lot #R02A005; resomer R104, Poly(D,L-lactide), Boehringer Ingelheim Corp. Lot #290588; resomer R202S, Poly(D,L-lactide), Boehringer Ingelheim Corp. Lot #Res-0380; and resomer R202H, Poly(D,L-lactide), Boehringer Ingelheim Corp. Lot #1011981.

Phosphate buffered saline (PBS) solution was prepared by adding two packets of PBS (Sigma catalog #P-3813) granules and two grams of sodium azide (extra pure grade, 99.0% by cerimetry) to a 2-L volumetric flask and adding deionized water.

The polymeric component and macromolecule component were blended using a Turbula shaker type T2F (Glenn Mills, Inc.). An F. Kurt Retsch GmbH& Co model MM200 ball mill was used with small stainless steel containers to mill particles of various sizes. A modified Janesville Tool and Manufacturing Inc. pneumatic drive powder compactor, model A-1024 was used to compact the mixture. Extrusion of the mixture was accomplished using a custom built piston extruder produced by APS Engineering Inc with a Watlow 93 temperature controller and thermocouple. A Mettler Toledo MT6 balance was used to weigh the drug delivery systems. Absorption characteristics were measured using a Beckman Coulter DU 800 UV/Vis spectrophotometer was used in conjunction with system and application software V 2.0. Coomassie plus protein assay reagent by Pierce Biotechnology was used, as supplied in The Better Bradford Assay Kit.

The macromolecule was stored at room temperature with minimal light exposure, and polymers were stored at 5° C. and allowed to equilibrate to room temperature prior to use. Formulations, listed in Table 3, were blended in a stainless steel mixing capsule with two stainless steel balls and placed in a Retsch mill at 30 cpm or Turbula blender at 96 RPM for 5 to 15 minutes. Depending on the starting materials, formulations underwent four to six blending cycles at 5 to 15 minutes each. Between blending cycles, a stainless steel spatula was used to dislodge material from the inside surfaces of the mixing vessel. Formulation ratios and extrusion temperatures for all formulations are listed in Table 3.

TABLE 3

BSA formulations and extrusion conditions

| Formulation # | BSA Loading (%) | Polymer | Extrusion Temp. (C.) |
|---|---|---|---|
| 1. Original Formulation Set | | | |
| 7409-098 | 30 | Resomer R104* | 57 |
| 7409-099 | 50 | Resomer R104 | 61 |
| 7409-100 | 30 | Resomer RG502H** | 63 |

TABLE 3-continued

BSA formulations and extrusion conditions

| Formulation # | BSA Loading (%) | Polymer | Extrusion Temp. (C.) |
|---|---|---|---|
| 7409-101 | 50 | Resomer RG502H | 74 |
| 7409-102 | 30 | Resomer RG502† | 75 |
| 7409-103 | 50 | Resomer RG502 | 78 |
| 7409-107 | 30 | Resomer RG752†† | 75 |
| 7409-108 | 50 | Resomer RG752 | 79 |
| 7409-109 | 30 | Resomer R202H± | 74 |
| 7409-110 | 30 | Resomer R202S‡ | 68 |
| 2. Lower Loading Formulation set | | | |
| 7409-139 | 20 | Resomer R104 | 53 |
| 7409-140 | 10 | Resomer R104 | 54 |
| 7409-143 | 5 | Resomer R104 | 50 |
| 7409-144 | 20 | Resomer RG752 | 69 |
| 7409-145 | 10 | Resomer RG752 | 68 |
| 7409-152 | 10 | Resomer RG502 | 72 |
| 7409-153 | 5 | Resomer RG752 | 72 |
| 3. Variations of Resomer RG752 Formulation Set | | | |
| 7409-163 | 10 | Resomer RG752 | 70 |
| 7409-164 | 10 | Resomer RG752 | 78 |
| 7409-165 | 15 | Resomer RG752 | 72 |
| 7409-166 | 8 | Resomer RG752 | 73 |
| 7409-167 | 5 | Resomer RG752 | 73 |
| 4. Milled Materials Formulation Set | | | |
| 7409-173 | 10 | Resomer RG752 | 72 |
| 7409-174 | 5 | Resomer RG752 | 72 |
| 7409-175 | 10 | Resomer R104 | 70 |
| 7409-176 | 5 | Resomer R104 | 63 |

*Resomer R104 = Boehringer Ingelheim Poly(L-lactide), MW = 2000
**Resomer RG502H = Boehringer Ingelheim 50:50 Poly(D,L-lactide-co-glycolide) with acid ends, IV = 0.16
†Resomer RG502, RG502S = Boehringer Ingelheim 50:50 Poly(D, L-lactide-co-glycolide), IV = 0.16-0.24
††Resomer RG752 = Boehringer Ingelheim 75:25 Poly(D, L-lactide-co-glycolide), IV = 0.2(dl/g)
±Resomer R202H = Boehringer Ingelheim Poly (L-Lactide) with acid ends, IV = 0.2
‡Resomer R202S = Boehringer Ingelheim Poly (L-Lactide), IV = 0.2

Materials were milled using a Retsch ball mill. Approximately one gram was loaded into a stainless steel vessel with one or two stainless steel balls. The material was milled at 20-40 cycles per second for up to five minutes. When the mill stopped, the vessel was opened and any material that was adhered to the inside surfaces was mechanically loosened with a spatula. Milling and loosening was repeated until the raw material was a fine powder.

A die with a 720 μm opening was attached to a stainless steel barrel, and the powder compactor was set to 50 psi. The barrel was inserted into the powder compactor assembly. Small increments of powder blend were added to the barrel using a stainless steel funnel. After each addition, the powder was compacted by actuating the compactor. This process was repeated until the barrel was full or no more powder remained A piston extruder was set to temperature and allowed to equilibrate. The extrusion temperature was chosen based on drug loading and polymer excipient. Formulations extrusion temperatures were between 58° C. and 78° C. (Table 3). After the extruder temperature equilibrated, the barrel was inserted into the extruder, and a thermocouple was inserted to measure the temperature at the surface of the barrel. After the barrel temperature equilibrated, the piston was inserted into the barrel, and the piston speed was set at 0.0025 in/min. The first 2-4 inches of extrudate was discarded. Afterwards, 3-5-inch pieces were cut directly into a centrifuge tube. Samples were labeled and stored in a sealed foil pouch containing desiccant.

A calibration plot was created by diluting a known standard to the range of 2 to 20 μg/mL, adding coomassie dye, and measuring the absorbance at 595 nm (FIG. 1).

Six 1 mg (+/-10%) samples were cut from each formulation. They were weighed and placed individually into 40-mL sample vials. Twenty milliliters of release medium was added to each vial and all vials were placed into a shaking water bath set at 37° C. and 50 RPM. At each time point, 1 mL was taken from each vial for analysis and placed in a 4-mL vial. The remaining solution was disposed of, and 20 mL of new release media was added to each vial. One milliliter of room temperature Coomassie stock solution was added to each vial and to two vials containing 1 mL of release medium (standards). All vials were capped and left on an orbital shaker for at least thirty minutes. Samples were analyzed using a Beckman Coulter DU 800 UV/Vis Spectrophotometer in single wavelength mode at 595 nm. Sample concentrations were calculated from a calibration plot of absorbance vs. wavelength using the extinction coefficient calculated from the Beer-Lambert law. The total amount of BSA released was calculated from the sample concentration. Table 4 lists the percent of BSA released with time for all formulations.

TABLE 4

Release data for BSA formulations.

| | Extrusion Conditions | | | Average Percent of Total BSA Released | | | | | |
|---|---|---|---|---|---|---|---|---|---|
| Lot # | BSA Loading (%) | Polymers | Temp. (C.) | 1 Day | 1 Week | 2 Weeks | 3 Weeks | 4 Weeks | 5 Weeks |
| 1. Original Formulation Set | | | | | | | | | |
| 7409-098 | 30 | Resomer R104 | 57 | 73 | 79 | 86 | 87 | 91 | |
| 7409-099 | 50 | Resomer R104 | 61 | 74 | 79 | 82 | 83 | 85 | |
| 7409-100 | 30 | Resomer RG502H | 63 | 87 | 97 | 97 | | | |
| 7409-101 | 50 | Resomer RG502H | 74 | 77 | 82 | 85 | 86 | 87 | |
| 7409-102 | 30 | Resomer RG502 | 75 | 87 | 89 | 100 | | | |
| 7409-103 | 50 | Resomer RG502 | 78 | 83 | 87 | 88 | 91 | | |
| 7409-107 | 30 | Resomer RG752 | 75 | 75 | 86 | 88 | 92 | | |
| 7409-108 | 50 | Resomer RG752 | 79 | 81 | 90 | 92 | 92 | | |
| 7409-109 | 30 | Resomer R202H | 74 | 100 | 109 | | | | |
| 7409-110 | 30 | Resomer R202S | 68 | 100 | 102 | | | | |
| 2. Lower Loading Formulation set | | | | | | | | | |
| 7409-139 | 20 | Resomer R104 | 53 | 99 | 101 | | | | |
| 7409-140 | 10 | Resomer R104 | 54 | 129 | 134 | | | | |
| 7409-143 | 5 | Resomer R104 | 50 | 117 | 181 | | | | |
| 7409-144 | 20 | Resomer RG752 | 69 | 105 | 115 | | | | |
| 7409-145 | 10 | Resomer RG752 | 68 | 29 | 32 | 33 | 37 | | 49 |

TABLE 4-continued

Release data for BSA formulations.

| | Extrusion Conditions | | | Average Percent of Total BSA Released | | | | | |
|---|---|---|---|---|---|---|---|---|---|
| Lot # | BSA Loading (%) | Polymers | Temp. (C.) | 1 Day | 1 Week | 2 Weeks | 3 Weeks | 4 Weeks | 5 Weeks |
| 7409-152 | 10 | Resomer RG502 | 72 | 49 | 49 | | 57 | | |
| 7409-153 | 5 | Resomer RG752 | 72 | 53 | 53 | | 79 | | |
| 3. Variations of Resomer RG752 Formulation Set | | | | | | | | | |
| 7409-163 | 10 | Resomer RG752 | 70 | 53 | | 53 | | | |
| 7409-164 | 10 | Resomer RG752 | 78 | 52 | | 60 | | | |
| 7409-165 | 15 | Resomer RG752 | 72 | 76 | | 92 | | | |
| 7409-166 | 8 | Resomer RG752 | 73 | 63 | | 79 | | | |
| 7409-167 | 5 | Resomer RG752 | 73 | 28 | | 57 | | | |
| 4. Milled Materials Formulation Set | | | | | | | | | |
| 7409-173 | 10 | Resomer RG752 | 72 | 20 | 27 | 31 | 44 | 51 | |
| 7409-174 | 5 | Resomer RG752 | 72 | 6 | 20 | 25 | 51 | 69 | |
| 7409-175 | 10 | Resomer R104 | 70 | 37 | 47 | 55 | 74 | 83 | |
| 7409-176 | 5 | Resomer R104 | 63 | 58 | 82 | 83 | 109 | | |

The first ten formulations of BSA in biodegradable polymer varied the drug loading from thirty to fifty percent. Changing the loading from 50 to 30 percent did not decrease the BSA release.

Reducing the loading to 5%-20% reduced the one-day release in some of the formulations. Thus, as shown by Table 4, three of "Lower Loading Formulation Set" released slower than the "Original Formulation Set" (29%, 49%, and 53%). Formulation 7409-145, made with 10% BSA and 90% Resomer RG752 showed consistent sustained release through five weeks.

Mixing conditions and extrusion temperature have a large affect on release profile. Formulations, 7409-163 through 7409-167 were similar to formulation 7409-145, with only minor changes in mixing conditions, extrusion temperature, or BSA loading. The percent release after one day for formulations 7409-163 through 7409-167 was up to 76%. This indicated that changes in mixing, compacting, and extrusion conditions can have a preferential effect on the release profile. For example the only difference between formulation 7409-163 and formulation 7409-145 was the mixing procedure, yet the one-day percent release was 20% higher for 7409-163.

Figure 2:
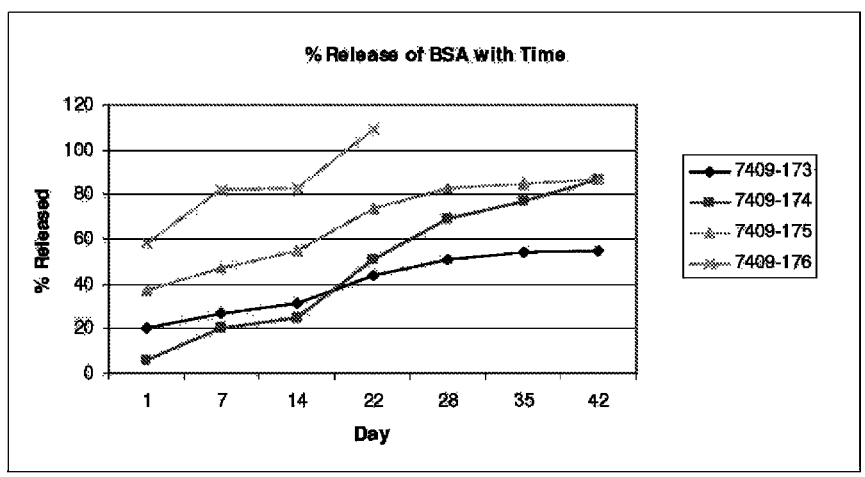
FIG. 2 is a release rate plot for BSA in a phosphate buffered saline (PBS) release medium, pH 7.4.

The fourth set of formulations incorporated powder milling of both the BSA and polymers. All raw materials looked fine and powdery before they were mixed together. Formulation 7409-173, with a 10:90 BSA:RG752 ratio released slowly. Only 20% of the BSA was released on after 1 day and only 44% had been released after three weeks (FIG. 2). Formulation 7409-174, with a 5:95 BSA:RG752 ratio released at a much slower rate than formulation 7409-153 or 7409-167, which were made from material that was not micronized but used in the same ratio.

Sustained release of bovine serum albumin from biodegradable polymers was achieved by modifying the percent BSA loading and the particle size of the starting materials. This experiment with bovine serum albumin determined that the loading in PLGA polymers of a macromolecule, such as a protein should be about ten percent or less in order to achieve controlled release of the macromolecule into a aqueous solution, such as for example the vitreous. This experiment also demonstrated that micronizing the polymer and the macromolecule (such as BSA) decreases the amount of the macromolecule that is released in the first day, that is reduces the burst effect. In addition, mixing and extrusion conditions may have a significant impact on the release profile of a macromolecule and, therefore, other highly soluble compounds as well.

This example also demonstrates that large macromolecules can retain their structure while incorporated into a polymeric drug delivery system that is processed at elevated temperatures. For example, BSA having a molecular weight of about 80 kDa retains its structure in an extruded drug delivery system. As shown in Table 4 and based on the calibration curve of FIG. 1 and the release profile method disclosed herein, it can be concluded that the structure and therefore biological activity of the macromolecule was preserved since the BSA remained in solution upon release into the PBS release medium. It was apparent that the BSA was in solution in the release medium because there was no precipitate and since the in vitro release profile determination method was effective and requires the BSA to be in solution. Additionally, when the in vitro release medium solution was heated to 80° C. the BSA denatured and precipitated out (i.e. lost its biological activity).

The BSA used in the implants made and evaluated in this study can be easily replaced with a human serum albumin (HSA) or with a recombinant albumin (rA) such as a recombinant human serum albumin (rHSA) with similar results. Thus, human serum albumin (plasma derived) is available commercially from various sources, including, for example, from Bayer Corporation, pharmaceutical division, Elkhart, Ill., under the trade name Plasbumin®. Plasbumin® is known to contain albumin obtained from pooled human venous plasma as well as sodium caprylate (a fatty acid, also known as octanoate) and acetyltryptophan ("NAT"). See e.g. the Bayer Plasbumin®-20 product insert (directions for use) supplied with the product. The caprylate and acetyltryptophan in commercially available human serum albumin are apparently added by FDA requirement to stabilize the albumin during pasteurization at 60 degrees C. for 10 hours prior to commercial sale. See e.g. Peters, T., Jr., *All About Albumin Biochemistry, Genetics and Medical Applications*, Academic Press (1996), pages 295 and 298. Recombinant human albumin is available from various sources, including for example, from Bipha Corporation of Chitose, Hokkaido, Japan, Welfide Corporation of Osaka, Japan, and from Delta Biotechnology, Nottingham, U.K., as a yeast fermentation product, under the trade name Recombumin®.

It is known to express recombinant human serum albumin (rHSA) in the yeast species *Pichia pastoris*. See e.g. Kobayashi K., et al., *The development of recombinant human serum albumin*, Ther Apher 1998 November; 2(4):257-62, and; Ohtani W., et al., *Physicochemical and immunochemical properties of recombinant human serum albumin from Pichia pastoris*, Anal Biochem 1998 Feb. 1; 256(1):56-62. See also U.S. Pat. No. 6,034,221 and European patents 330 451 and 361 991. A clear advantage of using a rHSA in an intraocular implant (for example to stabilize an active agent, such as a biologically active macromolecule [such as a protein], which accompanies the rHSA in the implant) is that it is free of blood derived pathogens.

Example 6A

In vitro Release of Antibody from a Biodegradable Implant

An in vitro experiment was carried out with another macromolecule, a VEGF inhibitory Fab antibody fragment (ImClone IMC 1121 Fab, incorporated into a poly(lactide-co-glycolide) polymer implant DDS (made with the PLGA resomer RG 752) used was in a manner substantially similar to the manner described in Example 6 above for BSA.

The Fab fragment was provided in a lyophilizate in trehalose. Size exclusion HPLC was used to determine the concentration of the Fab fragment in the lyophilizate after reconstitution.

A DDS formulation was made as follows. The following ingredients were mixed:

| Ingredient | % w/w |
|---|---|
| Fab | 5.45 |
| Dried PBS | 7.13 |
| trehalose | 3.00 |
| Resomer RG 752 | 84.4 |

Each DDS was approximately 5 mm in length and 1 mg in weight. Five identical DDS particles were placed in 5 ml polypropylene vials in 1 ml of 1×PBS, and shaken at 42° C. (accelerated temperature study) in a water bath at 50 rpm. Samples of the BSA "release media" were taken at 5, 7, 14, and 35 days, and a fresh 1 ml of PBS was used to replace the release media, which was used for subsequent ELISA and HPLC assays. Control DDS particles were also made with added BSA to reduce non-specific binding of the Fab to the tube and pipettes.

The receptor media taken from the incubations were assayed both by size exclusion HPLC and using ELISA (enzyme-linked immunosorption assay).

In the ELISA assay, microplates were coated with the capture antibody (a recombinant KDR-AP-streptavidin antibody that specifically binds the undenatured Fab fragment). Either Fab standards or the test solutions are added to the plates, to which is then added the detection antibody (a goat-antihuman HRP (horseradish peroxidase) conjugate specific to the kappa light chain constant regions of the Fab fragment). After permitting time for binding of the Fab fragment to the microplates via the coated antibody, the plates are gently washed and developed using tetramethylbenzidine and hydrogen peroxide to yield a colored product. The samples are subjected to spectrophotometric analysis to quantify the amount of bound Fab using a set of standard concentrations of the Fab.

HPLC (high performance liquid chromatography) analysis was done using a size exclusion (SE) HPLC column having a separation range, and under pump rate conditions permitting the separation of the antibodies and Fab fragments and monitoring absorbance by the eluate at 280 nm. The amount of Fab is determined using a set of standards.

FIG. 4 is a graph showing the Fab release from the DDS under these in vitro conditions. The open and closed circles graphs show the assay data based on the SE HPLC assay, and the open and closed squares show release of the Fab from the DDS based upon ELISA. As can be seen, between about 7% and 10% of the Fab fragment is released in the first 2 days. A relatively constant rate of release is seen in the first 20 days, at which time between about 12% (ELISA) and 16% (HPLC) of the Fab has been released from the DDS. By 35 days following the start of the experiment between about 37% (HPLC) and 25% (ELISA) of the Fab fragment has been released. Additionally, under both ELISA and HPLC, the addition of BSA prevents the non-specific adsorption of the Fab to loci other than the antibodies used in the assay (such as the microtiter dish), resulting in higher recovery of the Fab fragment from the BSA-containing samples.

Importantly, FIG. 4 and subsequent data obtained shows that the IMC-1121 Fab antibody retained binding activity (as measured by ELISA) after 42 days incubation. The HPLC data are from size exclusion chromatography monitored by absorbance at 280 nm. These data represent total soluble protein, and the presence of a single peak on chromatograms obtained showed no detectable aggregation in the release media. Significantly, the antibody studied retained its biological activity after incorporation into and release from the biodegradable polymer of the DDS The Figure data show that this DDS formulation had a biphasic release characteristic, with phase 1 (day 1 through day 20) exhibiting a rate of release of about 0.2% per day, and Phase 2 (day 20 through day 35) showing a rate of approximately 0.8% to 1% per day. Only two end points were used for determining the Phase 2 rate, thus the rate of Phase 2 may be somewhat greater than this if the beginning of Phase 1 occurs at a point later than 20 days and/or the ends before day 35.

Additionally, the ELISA and HLPC data demonstrated that the Fab fragment has maintained its tertiary structure under the fabrication and assay conditions set forth herein. Fidelity of tertiary structure is important in the maintenance of binding affinity; thus the ELISA data shown that the vast majority of the Fab remains in a bioactive conformation.

In conclusion the IMC-1121 Fab antibody can be freeze dried with trehalose, blended with a biodegradable PLGA polymer, extruded into a DDS (at about 70° C.—see Table 3.) suitable for intraocular administration, the antibody released into phosphate buffered saline over a period of at least 42 days, and the antibody can still retain most if not all of its binding activity against the VEGFR-2 receptor (KDR). This experiment shows that a PLGA biodegradable implant suitable for intraocular (such an intravitreal) administration with sustained release of an antibody active agent for treating a VEGF mediated condition can be successfully made.

Example 7

Polymeric Drug Delivery Systems Containing Ranibizumab

Drug delivery systems are made by combining ranibizumab and PLGA at approximately 1:1 ratio. The mixture of ranibizumab and PLGA are processed and extruded, as described in Example 1, Example 6 or Example 6A above. Implants are formed from the extruded material. Implants having a total weight of about 1 milligram comprise about 500 micrograms of ranibizumab and about 500 micrograms of PLGA. Implants having a total weight of about 2 milligrams comprise about 1000 micrograms of ranibizumab and about 1000 micrograms of PLGA. These implants are stored in sterile conditions.

In vitro release testing, as described in Example 6, indicates that over the life of the implant in the release medium, the ranibizumab is released from the implant at a rate from about 0.3 micrograms per day to about 30 micrograms per day.

In vivo release testing is performed by injecting an implant into the vitreous of one eye of a plurality of rabbits. Vitreal samples are obtained from the rabbits at different time points after injection. The samples are measured for ranibizumab content. The data are examined to estimate the release rate or delivery rate of the ranibizumab from the implant. In certain implants, intravitreal release rates are observed that are similar to the in vitro release rates described above. Other implants are associated with greater release rates. In addition, clearance of the ranibizumab from the vitreous can vary. For example, as described above, some implants are associated with clearance rates 12 mL/day. Other implants are associated with clearance rates of less than 1 mL/day. Ranges of clearance rates of these implants can vary from about 0.4 mL/day to about 0.8 mL/day.

A 1 mg implant comprising 500 micrograms of ranibizumab is inserted in the vitreous, near the retina, of each eye of a patient who has been diagnosed with macular edema and neovascularization. Ophthalmic examination reveals that macular edema appears to noticeably decrease within about one month after the procedure. Further examination reveals that edema is substantially reduced within about six months after the procedure, and that neovascularization has not increased since the procedure. The patient reports no further loss of vision and reduced pain in the eye. Intraocular pressure also appears to be reduced. Annual follow-up examinations that reveal the patient does not have macular edema or further neovascularization indicate that the implant successfully treated the patient's ocular conditions.

Example 8

Polymeric Drug Delivery Systems Containing Fab IMC 1121

Drug delivery systems are made by combining the monoclonal antibody fragment, Fab IMC 1121 (ImClone Systems) and PLGA at approximately 1:10 ratio. The mixture of Fab IMC 1121 and PLGA are processed and extruded, as described in Example 1, Example 6 or Example 6A above. Implants are formed from the extruded material. Each implant weighs about 1 milligram, and therefore, each implant comprises about 100 micrograms of Fab IMC 1121 and about 900 micrograms of PLGA. These implants are stored in sterile conditions.

In vitro release testing, as described in Example 6, indicates that over the life of the implant in the release medium, the Fab IMC 1121 is released from the implant at a rate from about 0.06 micrograms per day to about 5.6 micrograms per day.

In vivo release testing is performed by injecting an implant into the vitreous of one eye of a plurality of rabbits. Vitreal samples are obtained from the rabbits at different time points after injection. The samples are measured for Fab IMC 1121 content. The data are examined to estimate the release rate or delivery rate of the Fab IMC 1121 from the implant. Intravitreal release rates are observed that are similar to the in vitro release rates described above.

A 1 mg implant comprising 100 micrograms of Fab IMC 1121 is inserted in the vitreous, near the retina, of each eye of a patient who has been diagnosed with glaucoma, and is experiencing macular edema and neovascularization. The implant appears to provide therapeutic benefits for at least ninety days after placement in the eye. Decreased pain reported by the patient, and examination by a physician indicate that the symptoms associated with the glaucoma, including the edema, begin to subside within about three months. The patient reports no further loss of vision and reduced pain in the eye. Intraocular pressure also appears to be reduced. Annual follow-up examinations that reveal the patient does not have macular edema or further neovascularization indicate that the implant successfully treated the patient's ocular conditions.

Example 9

Polymeric Drug Delivery Systems Containing F200 Fab

Drug delivery systems are made by combining the monoclonal antibody fragment, F200 Fab and PLGA at approximately 1:5 ratio. The mixture of F200 Fab and PLGA are processed and extruded, as described in Example 1, Example 6 or Example 6A. Implants are formed from the extruded material. Each implant weighs about 1 milligram, and therefore, each implant comprises about 200 micrograms of F200 Fab and about 800 micrograms of PLGA. These implants are milled into microparticles which are stored in sterile conditions.

In vitro release testing, as described in Examples 6 and 6A, indicates that over the life of the microparticles in the release medium, the F200 Fab is released from the microparticles at a rate from about 0.13 micrograms per day to about 12.7 micrograms per day.

In vivo release testing is performed by injecting an amount of microparticles having a total weight of about 1 milligram into the vitreous of one eye of a plurality of rabbits. Vitreal samples are obtained from the rabbits at different time points after injection. The samples are measured for F200 Fab content. The data are examined to estimate the release rate or delivery rate of the F200 Fab from the microparticles. Intravitreal release rates are observed that are similar to the in vitro release rates described above.

A 1 mg sample of microparticles comprising 200 micrograms of F200 Fab is placed in the vitreous, near the retina, of each eye of a patient who has retinal detachment and associated neovascularization. The microparticles appear to provide therapeutic benefits for at least ninety days after placement in the eye. Decreased pain reported by the patient, and examination by a physician indicate that the ocular conditions improve within about three months. The patient reports no further loss of vision and reduced pain in the eye. Intraocular pressure also appears to be reduced. Annual follow-up examinations that reveal the patient does not show further detachment and neovascularization indicate that the drug delivery system successfully treated the patient's ocular conditions.

Example 10

Polymeric Drug Delivery Systems Containing Endostatin

Drug delivery systems are made by combining endostatin and PLGA at approximately 1:1 ratio. The mixture of endostatin and PLGA are processed and extruded, as described in Example 1, Example 6 or Example 6A above. Implants are formed from the extruded material. Drug delivery systems are formed which include about 35 milligrams of endostatin.

In vitro release testing, as described in Example 6, indicates that over the life of the systems in the release medium, the endostatin is released from the at a rate from about 20.9 micrograms per day to about 2090 micrograms per day. Substantially all of the endostatin is released in about 35 days.

In vivo release testing is performed by injecting a drug delivery system containing 35 milligrams of endostatin into the vitreous of one eye of a plurality of rabbits. Vitreal samples are obtained from the rabbits at different time points after injection. The samples are measured for endostatin content. The data are examined to estimate the release rate or delivery rate of endostatin from the microparticles. Intravitreal release rates are observed that are similar to the in vitro release rates described above.

A drug delivery system which comprises 35 milligrams of endostatin is placed in the vitreous of each eye of a patient who has choroidal neovascularization. The drug delivery systems are somewhat flexible so that they can be accommodated by the posterior segment of the eye. Therapeutic benefits are achieved within about thirty days after placement in the eye. After a single administration, annual follow-up examinations reveal the patient does not show further neovascular growth and indicates that the drug delivery system successfully treated the patient's ocular conditions.

Example 11

Polymeric Drug Delivery Systems Containing Angiostatin

Drug delivery systems which comprise about 350 micrograms of angiostatin can be produced similar to those systems described in any one of Examples 7-10, above. Such drug delivery systems release angiostatin at a rate from about 0.19 micrograms per day to about 18.5 micrograms per day. The release rates can be measured using in vitro and/or in vivo assays as described above. Placement of the angiostatin drug delivery systems into the vitreous of an eye provide therapeutic benefits, such as the treatment of neovascularization and the like, for at least about thirty days after a single administration. Improvements in patient function, such as vision and intraocular pressure, can be observed at longer time periods.

Example 12

Polymeric Drug Delivery Systems Containing PEDF

Drug delivery systems which comprise about 110 micrograms of PEDF can be produced similar to those systems described in any one of Examples 7-10, above. Such drug delivery systems release PEDF at a rate from about 0.06 micrograms per day to about 6.3 micrograms per day. The release rates can be measured using in vitro and/or in vivo assays as described above. Placement of the PEDF drug delivery systems into the vitreous of an eye provide therapeutic benefits, such as the treatment of neovascularization and the like, for at least about thirty days after a single administration. Improvements in patient function, such as vision and intraocular pressure, can be observed at longer time periods.

Example 13

Polymeric Drug Delivery Systems Containing VEGF Trap

Drug delivery systems which comprise about 310 micrograms of VEGF Trap can be produced similar to those systems described in any one of Examples 7-10, above. Such drug delivery systems release VEGF Trap at a rate from about 0.18 micrograms per day to about 17.7 micrograms per day. The release rates can be measured using in vitro and/or in vivo assays as described above. Placement of the VEGF Trap drug delivery systems into the vitreous of an eye provide therapeutic benefits, such as the treatment of neovascularization and the like, for at least about thirty days after a single administration. Improvements in patient function, such as vision and intraocular pressure, can be observed at longer time periods.

Example 14

Polymeric Drug Delivery Systems Containing A6

Drug delivery systems which comprise about 5 micrograms of A6 can be produced similar to those systems described in any one of Examples 7-10, above. Such drug delivery systems release A6 at a rate from about 0.003 micrograms per day to about 0.33 micrograms per day. The release rates can be measured using in vitro and/or in vivo assays as described above. Placement of the A6 drug delivery systems into the vitreous of an eye provide therapeutic benefits, such as the treatment of neovascularization and the like, for at least about thirty days after a single administration. Improvements in patient function, such as vision and intraocular pressure, can be observed at longer time periods.

Example 15

Polymeric Drug Delivery Systems Containing Cand5

Drug delivery systems which comprise about 86.1 milligrams of Cand5 can be produced similar to those systems described in any one of Examples 7-10, above. Such drug delivery systems release Cand5 at a rate from about 49.7 micrograms per day to about 4970 micrograms per day. The release rates can be measured using in vitro and/or in vivo assays as described above. Placement of the Cand5 drug delivery systems into the vitreous of an eye provide therapeutic benefits, such as the treatment of neovascularization and the like, for at least about thirty days after a single administration. Improvements in patient function, such as vision and intraocular pressure, can be observed at longer time periods.

Example 16

Polymeric Drug Delivery Systems Containing siRNA Z

Drug delivery systems which comprise about 86.1 milligrams of siRNA Z can be produced similar to those systems described in any one of Examples 7-10, above. Such drug delivery systems release siRNA Z at a rate from about 49.7 micrograms per day to about 4970 micrograms per day. The release rates can be measured using in vitro and/or in vivo assays as described above. Placement of the siRNA Z drug delivery systems into the vitreous of an eye provide therapeutic benefits, such as the treatment of neovascularization and the like, for at least about thirty days after a single adminis-

Example 17

Polymeric Drug Delivery Systems Containing Pegaptanib Sodium

Drug delivery systems which comprise about 250 micrograms of Pegaptanib Sodium can be produced similar to those systems described in any one of Examples 7-10, above. Such drug delivery systems release Pegaptanib Sodium at a rate from about 0.15 micrograms per day to about 14.5 micrograms per day. The release rates can be measured using in vitro and/or in vivo assays as described above. Placement of the Pegaptanib Sodium drug delivery systems into the vitreous of an eye provide therapeutic benefits, such as the treatment of neovascularization and the like, for at least about thirty days after a single administration. Improvements in patient function, such as vision and intraocular pressure, can be observed at longer time periods.

Example 18

Polymeric Drug Delivery Systems Containing Rapamycin

Drug delivery systems which comprise about 500 micrograms of rapamycin can be produced similar to those systems described in any one of Examples 7-10, above. Such drug delivery systems release rapamycin at a rate of about 5 micrograms per day. The release rates can be measured using in vitro and/or in vivo assays as described above. Placement of the rapamycin drug delivery systems into the vitreous of an eye provide therapeutic benefits, such as the treatment of uveitis, age related macular degeneration, and the like, for at least about ninety days after a single administration. Improvements in patient function and reductions in patient discomfort can be observed at longer time periods.

The examples described above demonstrate that the present drug delivery systems can contain biologically active macromolecule therapeutic agents, such as macromolecule therapeutic agents that retain their three-dimensional structure or a three dimensional structure which is associated with a therapeutic activity mediated by the therapeutic agent, when released from the drug delivery system under physiological conditions. The examples also demonstrate that systems which include anti-angiogenic or anti-neovascular macromolecule therapeutic agents, such as inhibitors of VEGF and VEGFR interactions, can effectively treat one or more ocular conditions, such as retinal and other posterior segment conditions, of patients in need thereof. Compared to existing products, the present systems provide effective treatment of one or more ocular conditions with fewer administrations of such compounds.

Example 19

Polymeric Drug Delivery Systems Containing Bevacizumab

Drug delivery systems are made by combining bevacizumab and PLGA at approximately 1:1 ratio. The mixture of bevacizumab and PLGA are processed and extruded, as described in Example 1, Example 6, or Example 6A above. Implants are formed from the extruded material. Implants having a total weight of about 1 milligram comprise about 500 micrograms of bevacizumab and about 500 micrograms of PLGA. Implants having a total weight of about 2 milligrams comprise about 1000 micrograms of bevacizumab and about 1000 micrograms of PLGA. Implants having a total weight of about 3 milligrams comprise about 1500 micrograms of bevacizumab and about 1500 micrograms of PLGA. These implants are stored in sterile conditions.

In vitro release testing, as described in Example 6, indicates that over the life of the implant in the release medium, the bevacizumab is released from the implant at a rate from about 0.3 micrograms per day to about 30 micrograms per day.

In vivo release testing is performed by injecting an implant into the vitreous of one eye of a plurality of rabbits. Vitreal samples are obtained from the rabbits at different time points after injection. The samples are measured for bevacizumab content. The data are examined to estimate the release rate or delivery rate of the bevacizumab from the implant. In certain implants, intravitreal release rates are observed that are similar to the in vitro release rates described above. Other implants are associated with greater release rates. In addition, clearance of the bevacizumab from the vitreous can vary. For example, as described above, some implants are associated with clearance rates of about 12 mL/day. Other implants are associated with clearance rates of less than about 1 mL/day. Ranges of clearance rates of these implants can vary from about 0.4 mL/day to about 0.8 mL/day.

A 2 mg implant comprising 1000 micrograms of bevacizumab is inserted in the vitreous, near the retina, of each eye of a patient who has been diagnosed with age related macular degeneration. Prior to treatment the patient's best corrected visual acuity is 20/100, and mean central retinal thickness is 300 microns.

The patient is given an identical intravitreal implant injection once every four weeks. At the end of 12 weeks of follow-up, the central retinal thickness is 177 microns, with a statistically significant decrease in retinal thickness is seen within 1 week after the first treatment.

Change in central retinal thickness correlates with an improvement in visual acuity, resulting in an 8-point change in visual acuity letter scores at 12 weeks. The extent of neovascularization does not increase since initiation of the procedure. The patient reports no further loss of vision and reduced pain in the eye during the 12 weeks of treatment.

Example 20

Polymeric Drug Delivery Systems Containing an anti-VEGFR-2 Fab fragment

The drug delivery system of this Example 20 contains a homogeneous blend of approximately 5% (w/v) Fab as described in Example 6A. The Fab antibody fragment is able to selectively bind vascular endothelial growth factor receptor (VEGFR-2), also called KDR.

Implants are formed from the extruded material. Implants having a total weight of about 1 milligram comprise about 50 micrograms of the anti VEGFR-2 Fab fragment and about 840 micrograms of PLGA. Implants having a total weight of about 2 milligrams comprise about 100 micrograms of the Fab fragment and about 1700 micrograms of PLGA. These implants are stored in sterile conditions.

In vitro release testing, as described in Example 6 and 6A, indicates that over the life of the implant in the release medium, the Fab is released from the implant at a rate from about 0.2 micrograms per day to between about 1 and 30 micrograms per day. This rate can be altered as needed depending upon the specific activity of the Fab fragment.

A 2 mg implant comprising 100 micrograms of the Fab fragment is inserted in the vitreous of each eye of a patient who has been diagnosed with age related macular degeneration. Prior to treatment the patient's best corrected visual acuity is 10/100, and mean central retinal thickness is 327 microns.

The patient is given an identical intravitreal implant injection once every six weeks. At the end of 12 weeks of follow-up, the central retinal thickness is 160 microns, while a statistically significant decrease in retinal thickness is seen within 6 weeks after the first treatment.

Change in central retinal thickness correlates with an improvement in visual acuity, resulting in a 7-point change in visual acuity letter scores at 12 weeks. The extent of neovascularization does not increase since initiation of the procedure. The patient reports no further loss of vision and reduced pain in the eye during the 12 weeks of treatment.

Example 21

Polymeric Drug Delivery Systems Containing C7S100

A batch of 1 mg DDS implants is formulated using 500 micrograms of the anti-VEGFR-2 fibronectin based "addressable" therapeutic binding molecule (FATBIM) termed Adnectin C7S100 in approximately a 1:1 ratio with PLGA. The release characteristics of this implant is evaluated using a similar protocol as that described in Examples 6 and 6A. The implant is made to have a release rate from about 0.19 micrograms per day to about 18.5 micrograms per day.

This implant is placed into the eye of a patient suffering from choroidal neovascularization. The implant is injected using a 22 gauge needle into the vitreous chamber in a solution of hyaluronic acid. Identical injections of implants are repeated every 8 weeks for 6 months. The patient's retina is monitored every two weeks throughout the treatment period. During the period of monitoring, no further progression of the neovascularization is seen, and visual acuity is observed to increase after approximately 8 weeks and remain elevated during the treatment period.

Similar results in other patients suffering from neovascularization are seen when using implants made using similar doses (standardized for specific activity) of the FATBIMs Adnectins CT-322 and C7C100.

Example 22

Polymeric Drug Delivery Systems Containing a Carbonic Anhydrase Inhibitorb

A sustained release drug delivery system ("DDS") can be made by combining the carbonic anhydrase inhibitor acetazolamide and a poly-lactide-co-glycolide polymer resin (PLGA). The implant can comprises from 10-20 wt % acetazolamide and from 80 wt % to 90 wt % poly (D,L,-lactide-co-glycolide) polymer (a PLGA). The implant can also contain a plasticizer such as 3-5 wt % PEG 400, or 5-10 wt % PEG 1000 (less wt % PLGA in that case) to help provide a desired in vivo first order (linear) release profile. The PLGA can be a 50:50 blend of 50 wt % lactide momomers and 50 wt % glycolide monomer, such as resomer RG502 PLGA (Boehringer Ingelheim, Wallingford, Conn.). The acetazolamide (melting point 258° C.) and the PLGA are accurately weighed and placed in a stainless steel mixing vessel. The vessel is sealed, placed on a Turbula mixer and mixed at a prescribed intensity, e.g., 96 rpm, and time, e.g., 10-15 minutes. The resulting powder blend is fed into a DACA Microcompounder-Extruder (DACA, Goleta, Calif.) and subjected to a temperature of about 100-115° C. and screw speed of 12 rpm. The filament is extruded into a guide mechanism and cut into 2 mm wide and 6 mm long, 1 mg weight filaments. The implant can release 1-2 mg acetaolamide/day over about a six month period when place in the vitreous, and the implant can be used to treat an ocular condition such a macular edema.

Thus, the 1 mg implant can be inserted in the vitreous, near the retina, of each eye of a patient who has been diagnosed with macular edema and neovascularization. Ophthalmic examination reveals that macular edema appears to noticeably decrease within about one month after the procedure. Further examination can reveal that edema is substantially reduced within about six months after the procedure, and that neovascularization has not increased since the procedure. The patient reports no further loss of vision and reduced pain in the eye. Intraocular pressure also appears to be reduced. Annual follow-up examinations that reveal the patient does not have macular edema or further neovascularization indicate that the implant successfully treated the patient's ocular conditions.

Other suitable carbonic anhydrase inhibitors which can be used in the DDS are brinzolamide, dorzolamide, methazolamide, and/or a thiophene sulfonamide.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A sustained release intraocular drug delivery system comprising: a first therapeutic component selected from the group consisting of acetazolamide, brinzolamide, dorzolamide, and methazolamide, a second therapeutic component selected from ranibizumab and bevacizumab, and a polymeric component comprising hyaluronic acid;
   wherein said system is formulated to release at least 10% of its active ingredient in the first two weeks following administration to the posterior chamber of a human eye.

2. The system of claim 1 wherein said system is formulated to release at least 20% of its active ingredient in the first two weeks following administration to the posterior chamber of a human eye.

3. The system of claim 1 wherein said system is formulated to release at least 30% of its active ingredient in the first two weeks following administration to the posterior chamber of a human eye.

4. The system of claim 1 wherein said system is formulated to release at least 40% of its active ingredient in the first two weeks following administration to the posterior chamber of a human eye.

5. The system of claim 1 in which said first therapeutic component is present in a viscous aqueous medium.

* * * * *